(12) United States Patent
Takeda

(10) Patent No.: US 11,096,670 B2
(45) Date of Patent: Aug. 24, 2021

(54) ULTRASOUND DIAGNOSTIC DEVICE AND ULTRASOUND IMAGE GENERATING METHOD

(71) Applicant: Konica Minolta, Inc., Tokyo (JP)

(72) Inventor: Yoshihiro Takeda, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 359 days.

(21) Appl. No.: 15/953,003

(22) Filed: Apr. 13, 2018

(65) Prior Publication Data

US 2018/0325493 A1 Nov. 15, 2018

(30) Foreign Application Priority Data

May 9, 2017 (JP) .............................. JP2017-092723

(51) Int. Cl.
  *A61B 8/08*   (2006.01)
  *A61B 8/06*   (2006.01)
  *A61B 8/00*   (2006.01)
  *G01S 7/52*   (2006.01)
  *G01S 15/89*  (2006.01)

(52) U.S. Cl.
  CPC .............. *A61B 8/5215* (2013.01); *A61B 8/06* (2013.01); *A61B 8/463* (2013.01); *A61B 8/488* (2013.01); *A61B 8/5207* (2013.01); *A61B 8/5246* (2013.01); *A61B 8/5269* (2013.01); *G01S 7/52077* (2013.01); *G01S 15/8977* (2013.01)

(58) Field of Classification Search
None
See application file for complete search history.

(56) References Cited

U.S. PATENT DOCUMENTS

2002/0169378 A1* 11/2002 Mo ..................... G01S 7/52084
                                                           600/437
2015/0320395 A1* 11/2015 Sato ......................... A61B 8/06
                                                           600/455
2017/0245832 A1*  8/2017 Kawata .................... A61B 8/06

FOREIGN PATENT DOCUMENTS

JP       2014158698 A     9/2014

OTHER PUBLICATIONS

Maudlin Jr. et al., "The singular value filter: a general filter design strategy for PCA-based signal separation in medical ultrasound imaging". IEEE Trans Med Imaging. Nov. 2011; 30(11): 1951-1964. (Year: 2011).*

(Continued)

*Primary Examiner* — Yi-Shan Yang
(74) *Attorney, Agent, or Firm* — Lucas & Mercanti, LLP

(57) ABSTRACT

An ultrasound diagnostic device including: a transmitter which outputs a driving signal for a C-mode image to an ultrasound probe sending and receiving ultrasound; a receiver which obtains a reception signal from the ultrasound probe; and a controller which: calculates an inner product value of packet data of the reception signal and a first orthonormal basis for each degree; sets a conversion function to convert the inner product value into a removal rate to remove a clutter component; converts the calculated inner product value into the removal rate for each degree by using the set conversion function; and generates image data from which a signal component of the C-mode image is removed according to the removal rate for each degree.

11 Claims, 16 Drawing Sheets

(56) References Cited

OTHER PUBLICATIONS

Bjærum et al., "Clutter filters adapted to tissue motion in ultrasound color flow imaging", IEEE Trans. Ultrasonics, Ferroelectrics and Frequency Control. 2002, vol. 49, No. 6, pp. 693-704. (Year: 2002).*
JPO, Office Action for the related Japanese Patent Application No. 2017-092723, dated Jan. 19, 2021, with English translation.
Steinar Bjarum et al., "Clutter Filters Adapted to Tissue Motion in Ultrasound Color Flow Imaging," IEEE Transactions on Ultrasonics, Ferroelectrics, and Frequency Control, Jun. 2002, vol. 49, pp. 693-704.

* cited by examiner

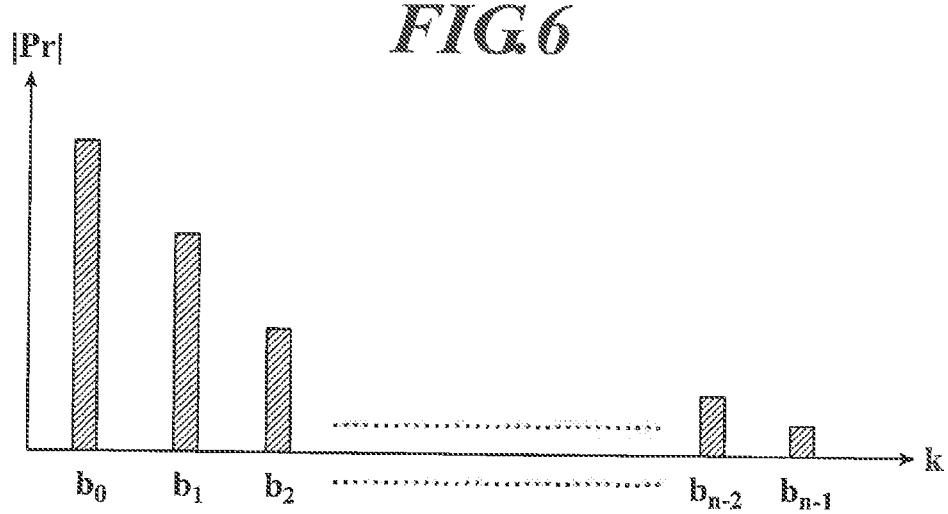

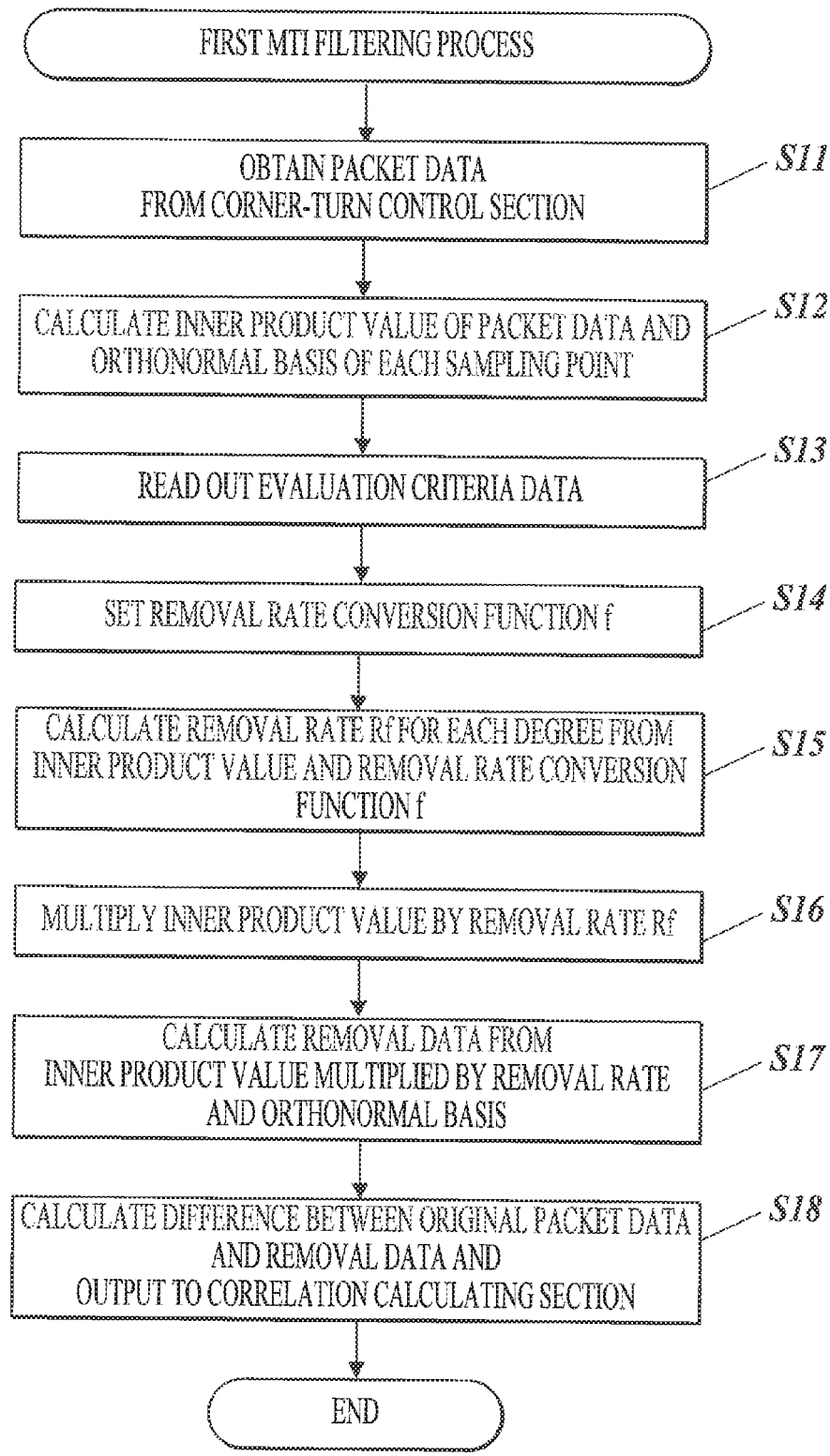

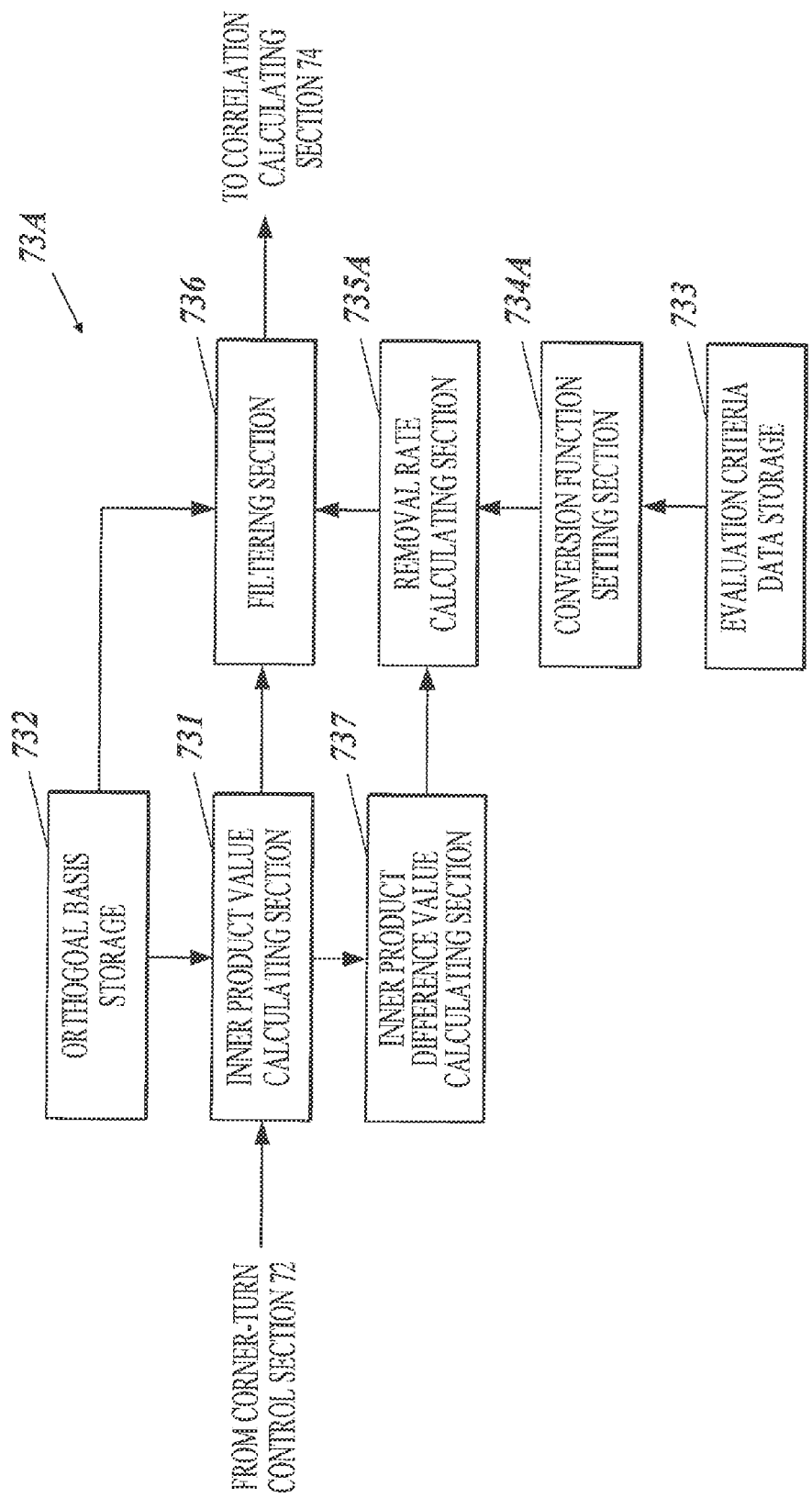

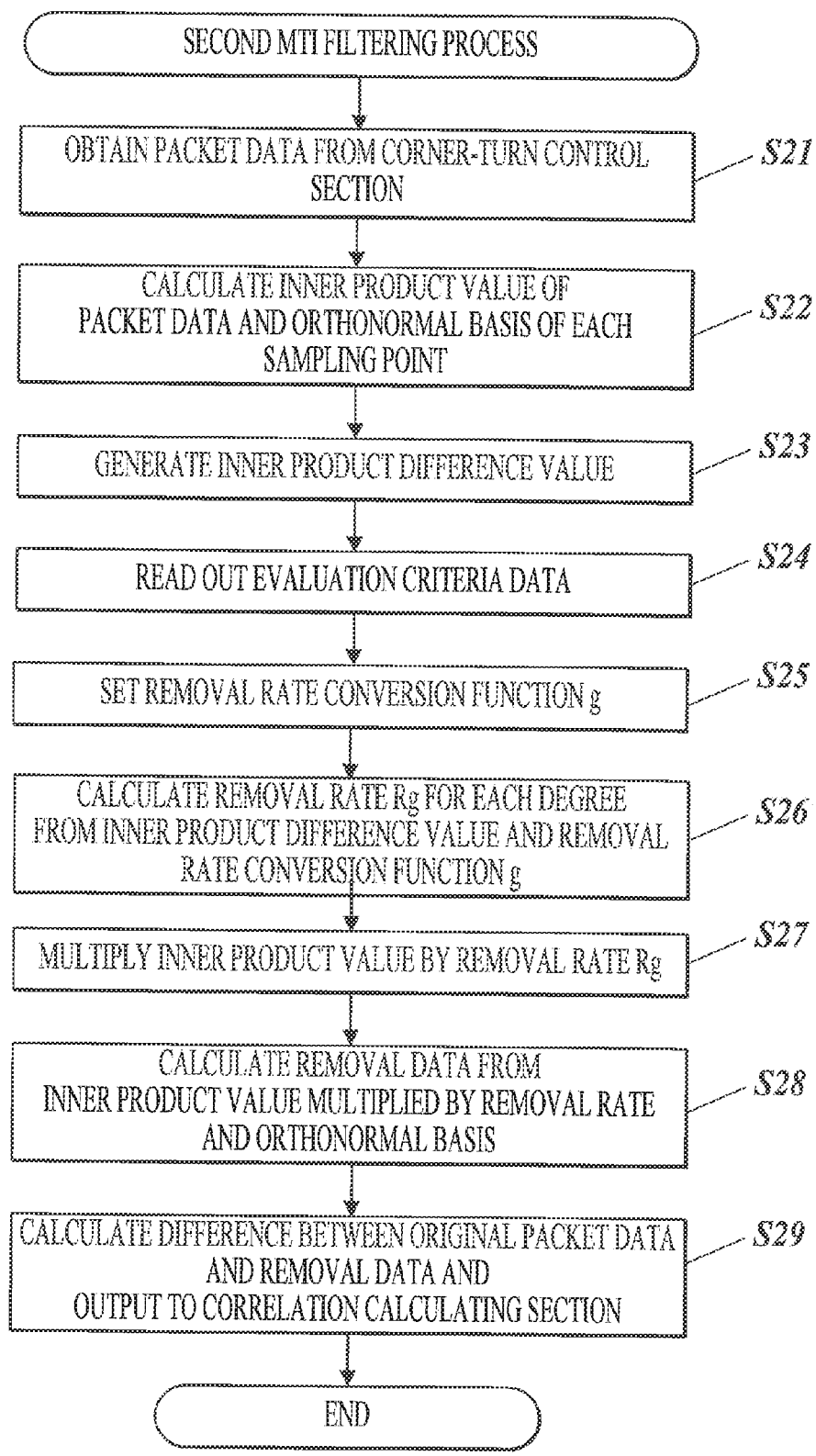

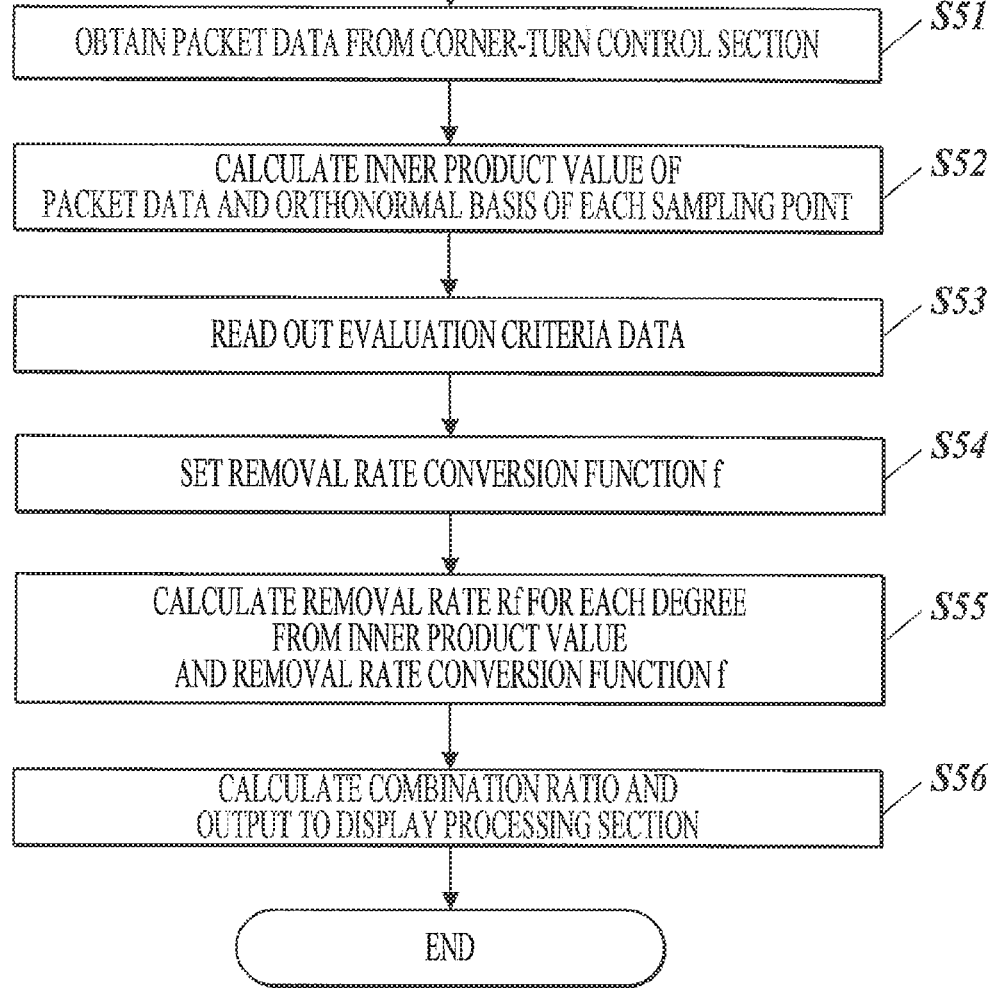
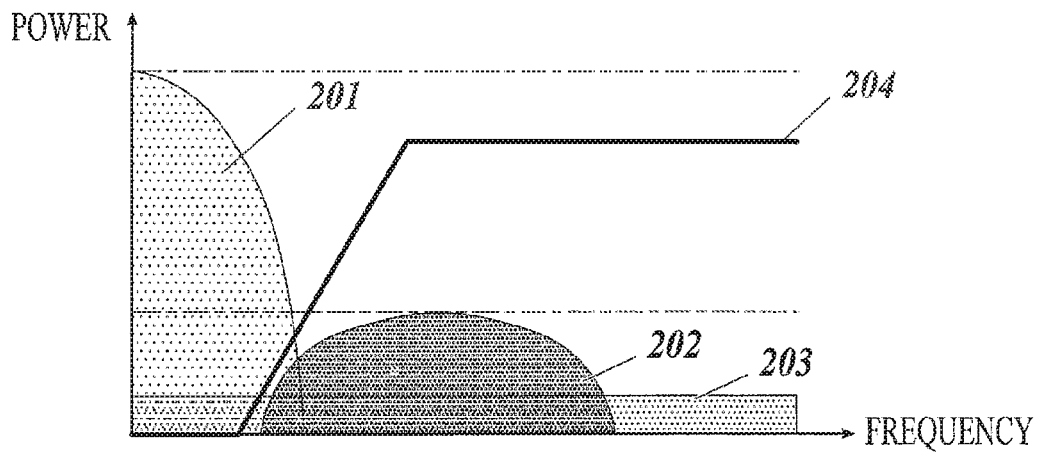

ULTRASOUND DIAGNOSTIC DEVICE AND ULTRASOUND IMAGE GENERATING METHOD

BACKGROUND

1. Technological Field

The present invention relates to an ultrasound diagnostic device and a method for generating ultrasound images.

2. Description of the Related Art

Ultrasound diagnosis is performed to obtain cardiac motions or fetal movements as ultrasound images by a simple operation of applying an ultrasound probe on the skin surface. Moreover, ultrasound diagnosis is safe enough to be repeated. There have been known ultrasound diagnostic devices used for ultrasound diagnosis which generate and display ultrasound images.

There also have been known some ultrasound diagnostic devices which generate and display C-mode (color flow mode, color Doppler mode) images by sending and receiving ultrasound to and from the subject, in which blood flow of the subject is colored and displayed by the Doppler method. FIG. 20 is a diagram showing the power-frequency characteristics of packet data and a conventional Moving Target Indication (MTI) filter.

In generating C-mode image data, obtained is the power-frequency characteristics of a Doppler signal (packet data) corresponding to a reception signal of ultrasound reflected on the subject. The packet data then can be divided into clutter components 201, blood flow components 202, and noise components 203, as shown in FIG. 20. The clutter components 201 are signal components of tissue movements of the subject. The blood flow components 202 are signal components of blood flow of the subject. The noise components 203 are signal components of system noise (random noise) specific to the device.

In the C-mode images, the clutter components 201 in the Doppler signal are removed by a MTI filter 204 to image the blood flow components. The MTI filter 204 is a high-pass filter which removes clutter components and extracts only Doppler shift components.

Recently, Hermitian transpose matrix has been used for the MTI filter. For example, there have been known ultrasound diagnostic devices using the MTI filter with eigenvectors of a filter matrix, in which clutters are suppressed by binary control of deciding a degree for the clutter components (RankCut degree) based on the size of each eigenvalue, removing the components for degrees lower than the RankCut degree and passing the components for degrees higher than the RankCut degree in the matrix operation which approximates and reduces clutter components as principal components after principal component analysis (see Japanese Patent Application Laid Open Publication No. 2014-158698).

The ultrasound diagnostic device described in Japanese Patent Application Laid Open Publication No. 2014-158698 decides an appropriate RankCut degree based on the eigenvalue of principal components (eigenvector) for each degree obtained by principal component analysis which is performed to the set of packet data. The signal to noise ratio (S/N) of the blood flow signal, however, cannot be maximized because the eigenvalue indicates nothing more than how much information is retained by the principal components and does not reflect the size of the clutters or the blood flow signal contained in individual packet data to be filtered by the MTI filter.

Therefore, its object is no more than avoiding a false image in the displayed images by equalizing the output sensitivity of filter by each region of the MTI filter. The technique is applicable only to the MTI filter which performs principal component analysis.

This means that appropriate images for blood flow observation cannot be always obtained in the ultrasound diagnosis device in Japanese Patent Application Laid Open Publication No. 2014-158698, because of a deviation in capacity of clutter removal or excessive removal of a blood flow signal depending on the region of interest in the packet data after the MTI filtering. It is also necessary for the operator to handle the characteristics of the MTI filter to obtain the optimized blood flow images.

SUMMARY

An object of the present invention is to optimize the S/N of a blood flow signal by suitably modifying the characteristics of MTI filtering to the packet data for the C-mode image.

To achieve at least one of the abovementioned objects, according to an aspect of the present invention, the ultrasound diagnostic device reflecting one aspect of the present invention comprises: a transmitter which outputs a driving signal for a C-mode image to an ultrasound probe sending and receiving ultrasound; a receiver which obtains a reception signal from the ultrasound probe; and a controller which: calculates an inner product value of packet data of the reception signal and a first orthonormal basis for each degree; sets a conversion function to convert the inner product value into a removal rate to remove a clutter component; converts the calculated inner product value into the removal rate for each degree by using the set conversion function; and generates image data from which a signal component of the C-mode image is removed according to the removal rate for each degree.

According to another aspect of the present invention, the ultrasound image generating method reflecting one aspect of the present invention comprises: a transmission step of outputting a driving signal for a C-mode image to an ultrasound probe sending and receiving ultrasound; a reception step of obtaining a reception signal from the ultrasound probe; an inner product value calculation step of calculating an inner product value of packet data of the reception signal and a first orthonormal basis for each degree; a conversion function setting step of setting a conversion function to convert the inner product value into a removal rate to remove a clutter component; a removal rate calculating step of converting the calculated inner product value into the removal rate for each degree by using the set conversion function; and a processing step of generating image data from which a signal component of the C-mode image is removed according to the removal rate for each degree.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 4 is a diagram showing the relation of input and output of an MTI filter;

FIG. 5 is a diagram showing a filter matrix using orthonormal basis;

FIG. 6 is a graph showing the distribution of an inner product value against degree of orthonormal basis;

FIG. 11 is a flow chart showing the process of first MTI filtering;

FIG. 12 is a block diagram showing the functional structure of a second MTI filter;

FIG. 14 is a flow chart showing the process of second MTI filtering;

FIG. 19 is a flow chart showing the process of calculating the combination ratio; and FIG. 20 is a diagram showing the power-frequency characteristics of packet data and a conventional MTI filter.

DETAILED DESCRIPTION OF EMBODIMENTS

Hereinafter one or more embodiments of the present invention will be described with reference to the drawings. However, the scope of the invention is not limited to the disclosed embodiments.

A first embodiment, first and second modification examples and a second embodiment of the present invention are described in detail with reference to the drawings.

First Embodiment

Figure 1:
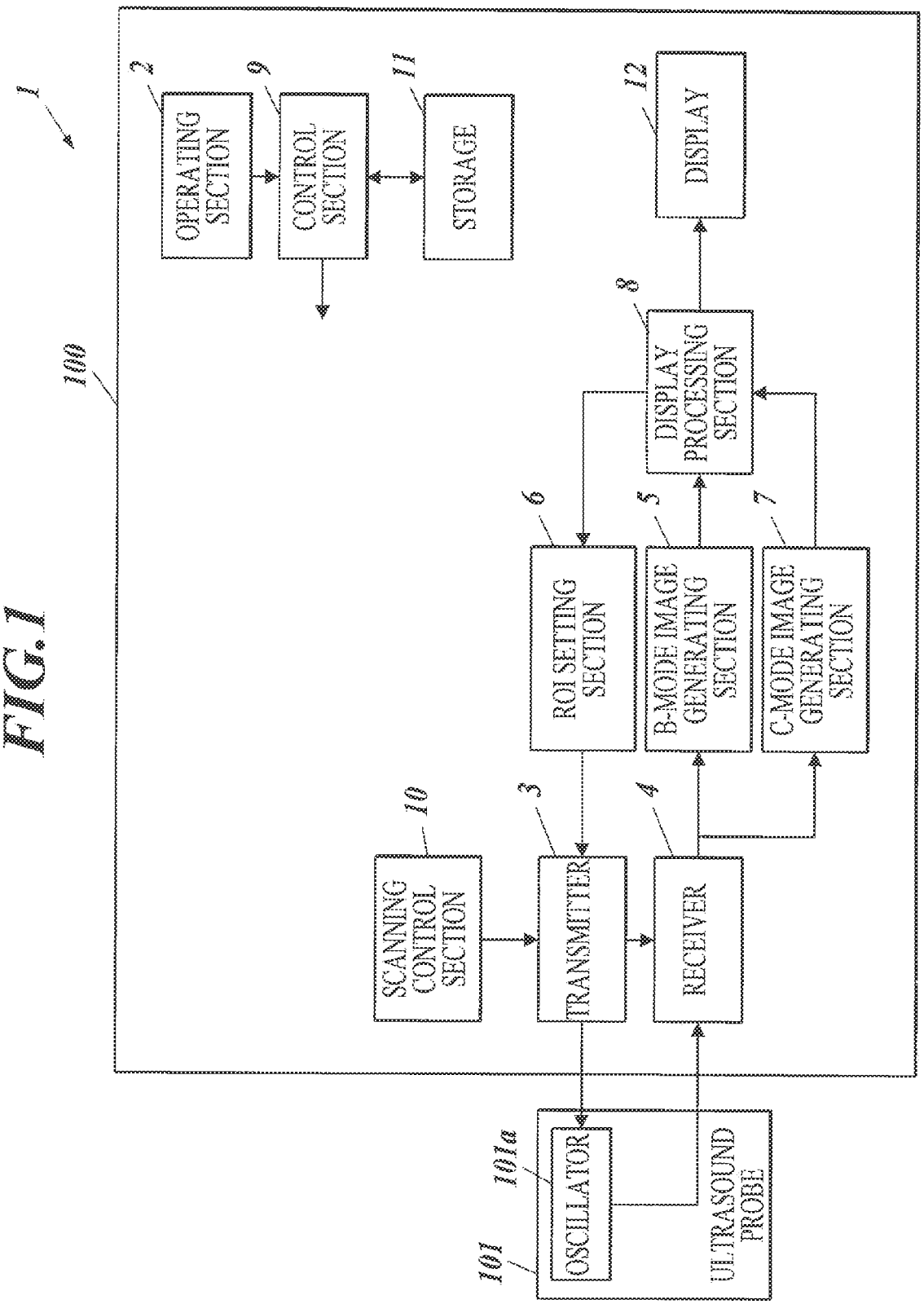
FIG. 1 is an outline block diagram showing the structure of an ultrasound diagnostic device 1 in a first embodiment of the present invention.
Figure 2:
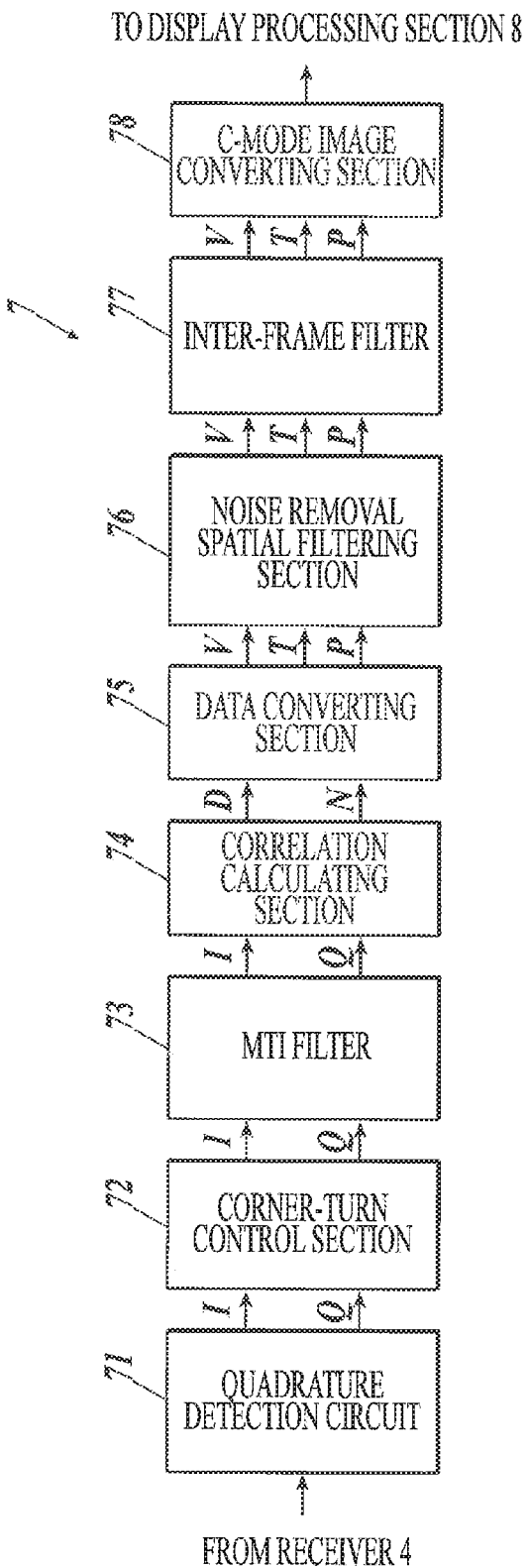
FIG. 2 is a block diagram showing the functional structure of a first C-mode image generating section.
Figure 3:
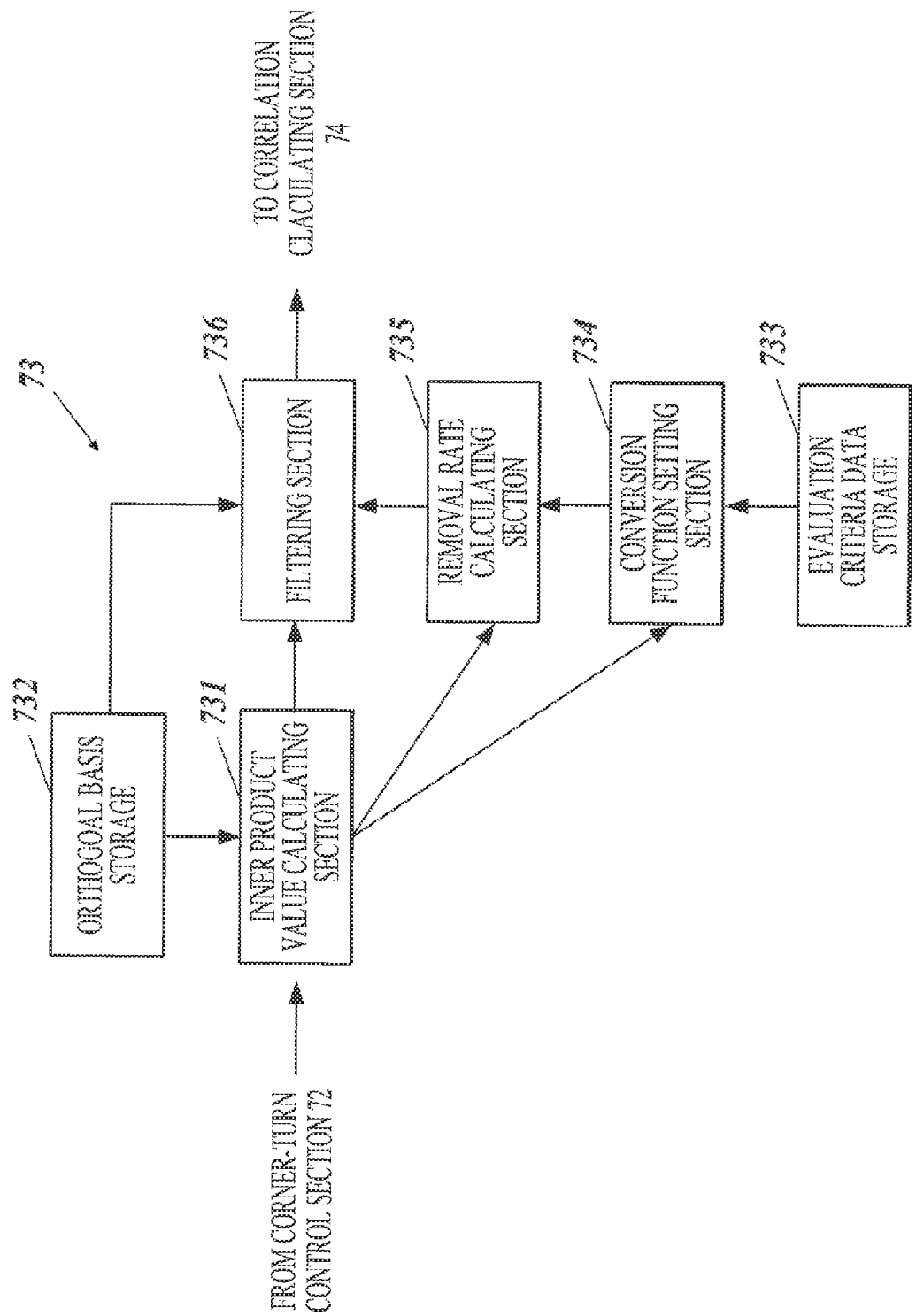
FIG. 3 is a block diagram showing the functional structure of a first MTI filter.

The first embodiment of the present invention is described hereinafter with reference to FIGS. 1 to 11. First, the device structure of the present embodiment is explained with reference to FIGS. 1 to 3. FIG. 1 is an outline block diagram showing the structure of an ultrasound diagnostic device 1 in the present embodiment. FIG. 2 is a block diagram showing the functional structure of a C-mode image generating section 7. FIG. 3 is a block diagram showing the functional structure of an MTI filter 73.

The ultrasound diagnostic device 1 in FIG. 1 is a device which is installed in medical facilities such as hospitals and generates ultrasound images of the subject such as the body of patient to be examined. An ultrasound probe 101 is connected to an ultrasound diagnostic device body 100 of the ultrasound diagnostic device 1.

The ultrasound diagnostic device body 100 incorporates an operating section 2, a transmitter 3, a receiver 4, a B (Brightness) mode image generating section 5, an ROI setting section 6, a C-mode image generating section 7, a display processing section 8 as a processing section, a control section 9, a scanning control section 10, a storage 11 and a display 12.

The ultrasound probe 101 has a plurality of oscillators (piezoelectric conversion elements) 101a arrayed one-dimensionally. The oscillators 101a respectively convert a driving signal (transmission electrical signal) from the transmitter 3 described later into ultrasound and generates an ultrasound beam. Accordingly, the operator can adapt an ultrasound beam to the inside of the subject to be examined by applying the ultrasound probe 101 to the surface of the subject. The ultrasound probe 101 receives the reflected ultrasound from the inside of the examination subject, converts the reflected ultrasound into a reception electrical signal with the oscillators 101a, and provides it to the receiver 4 described later.

In the present embodiment, a linear type ultrasound probe 101 with the oscillators 101a arrayed one-dimensionally is described. However, the description does not limit the configuration of the ultrasound probe 101. For example, a convex-type or sector-type ultrasound probe 101 with a plurality of oscillators 101a arrayed one-dimensionally, an ultrasound probe 101 with a plurality of oscillators 101a arrayed two-dimensionally, or an ultrasound probe 101 with a plurality of fluctuant oscillators 101a arrayed one-dimensionally may be used. The transmitter 3 can control under the control of the scanning control section 10 (the control section 9) the point and direction to adapt an ultrasound beam which the ultrasound probe 101 emits, by selecting the oscillators 101a of the ultrasound probe 101 to use and respectively modifying the timing and the value of voltage to impress to the oscillators 101a.

The ultrasound probe 101 may incorporate some of the functions of the transmitter 3 and the receiver 4 described later. For example, the ultrasound probe 101 may generate a driving signal inside the ultrasound probe 101 itself based on a control signal (hereinafter referred to as a transmission control signal) for generating a driving signal output from the transmitter 3, convert the driving signal into ultrasound with the oscillators 101*a* as well as reflected ultrasound into a reception electrical signal, and generate the reception signal described later inside the ultrasound probe 101 itself based on the reception electrical signal.

In general, the ultrasound probe 101 is connected electrically to the ultrasound diagnostic device body 100 via a cable, though not limited. For example, the ultrasound probe 101 may send and receive a transmission signal and a reception signal to and from the ultrasound diagnostic device body 100 via wireless communication. In such cases, however, it is needless to say that the ultrasound diagnostic device body 100 and the ultrasound probe 101 must have a communication section which allows wireless communication.

The operating section 2 receives an input from the operator and outputs a command according to the input of the operator to the ultrasound diagnostic device 1, precisely to the control section 9. The operating section 2 has a function which allows the operator to select from two modes: one to display only the B-mode image which expresses the amplitude of the reflected ultrasound by brightness (hereinafter referred to as B-mode), and another to display the C-mode (color flow mode) image superimposed on the B-mode image (hereinafter referred to as C-mode). And the operating section 2 has a function which accepts an input of ROI placement assignment by the operator for displaying the C-mode image on the B-mode image. The C-mode image is displayed in the following modes: V mode where the velocity and the direction of blood flow are displayed in color by the blood flow velocity V as a blood flow signal to show the blood flow status, P mode where the power of blood flow is displayed in color by the blood flow power P as a blood flow signal, and V-T mode where the velocity and the variance of blood flow are displayed in color by the blood flow velocity V and the blood flow variance T as a blood flow signal. When the operating section 2 accepts an input of C-mode from the operator, it also accepts an input of the mode for displaying. The modes for displaying the C-mode image may include T (variance) mode or dP (power with direction) mode. As described above, C-mode has color Doppler mode (represented by V-mode and V-T mode) and power Doppler mode (represented by P mode).

The transmitter 3 operates a transmission process, in which at least a driving signal is generated and the ultrasound probe 101 emits an ultrasound beam. For example, the oscillators 101*a* of the ultrasound probe 101 are driven as the transmitter 3 operates a transmission process of generating a transmission signal for the ultrasound probe 101 with the oscillators 101*a* to emit an ultrasound beam and providing the ultrasound probe 101 with a high-voltage transmission electrical signal (driving signal) which is generated at predetermined timings to the ultrasound probe 101 on the basis of the transmission signal. This is how the ultrasound probe 101 can emit an ultrasound beam to the subject by converting a transmission electrical signal into ultrasound.

When C-mode is on, the transmitter 3 operates a transmission process to display the C-mode image in addition to a transmission process to display the B-mode image under the control of the scanning control section 10. For example, after the electrical transmission signal to display the B-mode image is provided, the driving signal to display the C-mode image is provided to all directions (all lines) of ROI set by the ROI setting section 6 for n times (dozen times, for example, n=15) by each direction (each linear). The transmitter 3 sets additional information of the transmission process for the B-mode or C-mode image and provides the additional information to the receiver 4 in the transmission process.

The receiver 4 operates a reception process to generate a reception signal as an electrical RF (Radio Frequency) based on the reflected ultrasound under the control of the control section 9. The receiver 4 receives the reflected ultrasound with the ultrasound probe 101, and generates a reception signal (sound ray data) by A/D conversion and phasing addition by amplifying the reception electrical signal converted based on the reflected ultrasound.

The receiver 4, for example, obtains the additional information from the transmitter 3. Then when the obtained additional information is for the B-mode image, it is provided to the B-mode image generating section 5, and when the obtained additional information is for the C-mode image, it is provided to the C-mode image generating section 7. Hereinafter the reception signal for generating the B-mode image is referred to as "the B-mode reception signal," and the reception signal for generating the C-mode image as "the C-mode reception signal".

In the present embodiment, the receiver 4 provides a reception signal concerning a generated image frame to each block after sorting whether the reception signal is for the B-mode image or the C-mode image. However, it is not limited to this configuration. For example, the reception signal concerning the generated image frame may be sorted respectively in the B-mode image generating section 5 or the C-mode image generating section 7.

The B-mode image generating section 5, under the control of the control section 9, generates B-mode image data, and outputs it to the display processing section 8, in which the brightness conversion is executed by adjusting the dynamic range and the gain with envelope detection, logarithmic compression and so forth to the B-mode reception signal which is input from the receiver 4.

The C-mode image generating section 7, under the control of the control section 9, generates C-mode image data, and outputs it to the display processing section 8, according to the C-mode reception signal which is input from the receiver 4. The C-mode image generating section 7 is explained hereinafter with reference to FIG. 2. As shown in FIG. 2, the C-mode image generating section 7 has a quadrature detection circuit 71, a corner-turn control section 72, an MTI filter 73, a correlation calculating section 74, a data converting section 75, a noise removal spatial filtering section 76, an inter-frame filter 77, and a C-mode image converting section 78 as a C-mode image generating section.

The quadrature detection circuit 71 obtains (complex) Doppler signals I and Q by calculating the phase difference between a reference signal and the C-mode reception signal obtained by quadrature detection of the C-mode reception signal input from the receiver 4, under the control of the control section 9.

The corner-turn control section 72 stores the Doppler signals I and Q input from the quadrature detection circuit 71 in a memory (not shown in the drawings) after arranging them by each identical sound line in the depth direction from the ultrasound probe 101 to the subject and in the ensemble direction for continuation of n times of sending and receiving of ultrasound, and then reads out the Doppler signals I and Q for each unit depth in the ensemble direction, under the control of the control section 9.

The reception signal (Doppler signals I and Q) includes unnecessary information on blood vessel wall, tissues and so forth (clutter components), in addition to the signal components of blood flow necessary for generating the C-mode image. The MTI filter 73 removes the clutter components by filtering the Doppler signals I and Q input from the corner-turn control section 72, under the control of the control section 9.

The internal structure of the MTI filter 73 is explained hereinafter with reference to FIG. 3. As shown in FIG. 3, the MTI filter 73 has an inner product value calculating section 731 as an inner product value obtaining section, an orthogonal basis storage 732, an evaluation criteria data storage 733, a conversion function setting section 734, a removal rate calculating section 735 as a removal rate obtaining section, and a filtering section 736.

The MTI filter 73 is an MTI filter using orthonormal basis. The orthonormal bases are eigenvectors obtained by orthogonal polynomials or principal component analyses, for example. An example of the orthogonal polynomials is Legendre polynomials.

Hereinafter described is the computation of inner product value using orthonormal basis with reference to FIGS. 4 to 6. FIG. 4 is a diagram showing the relation of input and output of the MTI filter. FIG. 5 is a diagram showing the filter matrix using orthonormal basis. FIG. 6 is a graph showing the distribution of inner product value |Pr| against degree k of orthonormal basis.

The packet data Sp is defined by the complex number with a repetition of n consisting of the Doppler signals I and Q output from the corner-turn control section 72. The packet data Sp is denoted by n pieces of the input data, $x_0$, $x_1, \ldots, x_{n-1}$, where $x_0, x_1, \ldots, x_{n-1}$ are ordered chronologically, in ascending or descending order by time of generation.

As shown in FIG. 4, the input and output of the MTI filter that is a linear filter which does not have intermodulation between a clutter signal and a blood flow signal is expressed by the following formula (1).

$$y = Ax \quad (1)$$

y: the output vector defined by the packet data ($y_0$, $y_1, \ldots, y_{n-1}$) output from the MTI filter
A: the filter matrix (n×n)
x: the input vector defined by the input data $x_0, x_1, \ldots, x_{n-1}$ As shown in FIG. 5, the filter matrix A of the MTI filter using orthonormal basis is denoted by the filter matrix $A_{reg}$ in the following formula (2).

$$A_{reg} = b \times G \times b^H \quad (2)$$

b: the orthonormal basis (n×n matrix)
G: the gain matrix (n×n matrix)
$b^H$: the orthonormal basis (n×n matrix), the Hermitian transpose of b The orthonormal bases b and $b^H$ are eigenvectors obtained by various orthogonal polynomials or principal component analyses, for example. In the orthonormal basis b, degree increases in increments of column number. In the orthonormal basis $b^H$, degree increases in increments of row number. When eigenvectors obtained by principal component analysis as orthonormal bases are employed, the eigenvector with the largest eigenvalue is defined as 0 degree and the eigenvalue is ordered in a descending order as degree increments.

The input and output of the MTI filter 73 is given by the following formula (3), using decomposition to orthonormal basis of the formula (2).

$$Sp_{MTIed} = (I - bRb^H)Sp \quad (3)$$
$$= Sp - bRPr \quad (3A)$$

$Sp_{MTIed}$: the output packet data of the MTI filter 73 ($Sp_{MTIed}=[y_0, y_1, \ldots, y_{n-1}]$)
Sp: the input packet data of the MTI filter 73 (Sp=[$x_0$, $x_1, \ldots, x_{n-1}$]
I: the identity matrix
b: the orthonormal basis (orthonormal vector) in n dimensions (b=[$b_0, b_1, \ldots, b_{n-1}$])
$b^H$: the orthonormal basis (orthonormal vector) in n dimensions which is the Hermitian transpose of b ($b^H=[b_0^H, b_1^H, \ldots, b_{n-1}^H]$)
$b_1^H$, $b_k^H$: the vectors
R: the removal rate (diagonal matrix, R=[$R_0, R_1, \ldots, R_{n-1}$]
$R_k$: the removal rate for vector in k-th dimension)
Pr: the inner product value of $b^H$ and Sp
where $bb^H=I$ $(I-bRb^H)$ in the formula (3) corresponds to the filter matrix A. The formula (3) can be expressed by the following formula (4), when the degree k=0, 1, . . . , n−1.

$$y_k = x_k - b_k \cdot R_k \cdot b_k^H \cdot Sp \quad (4)$$

As shown in FIG. 6, the correlation between the inner product value |Pr| (the absolute value of the inner product Pr) and degree k of the orthonormal basis b is obtained. The inner product value |Pr| stands for the intensity of components for each degree of the orthonormal basis, like the intensity obtained by Fourier series expansion. In a case where the orthonormal basis b is an orthogonal polynomial, the inner product value |Pr| can be considered almost equal to the frequency characteristics, as higher frequency components appear for a larger degree k.

Figure 7A:
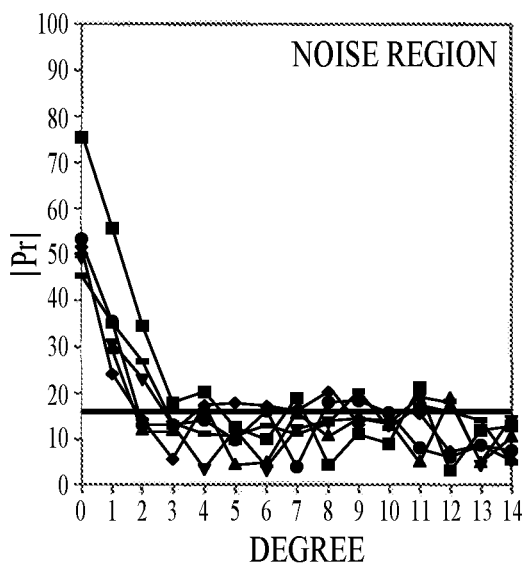
FIG. 7A is a graph showing the inner product value against degree in a noise region.
Figure 7B:
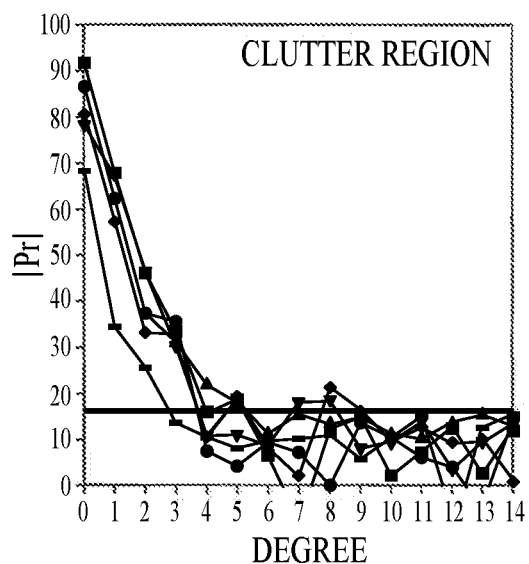
FIG. 7B is a graph showing the inner product value against degree in a clutter region.
Figure 7C:
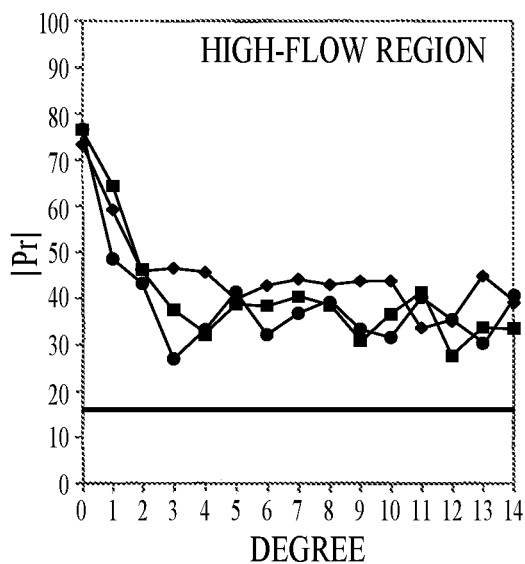
FIG. 7C is a graph showing the inner product value against degree in a high-flow region.
Figure 7D:
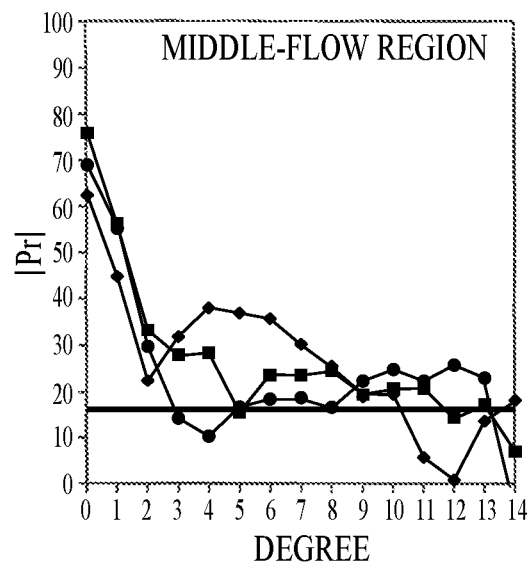
FIG. 7D is a graph showing the inner product value against degree in a middle-flow region.

The tendency of the inner product Pr for each degree is described hereinafter with reference to FIGS. 7A to 7D. FIG. 7A is a graph showing the inner product value |Pr| against degree in the noise region. FIG. 7B is a graph showing the inner product value |Pr| against degree in the clutter region. FIG. 7C is a graph showing the inner product value |Pr| against degree in the high-flow region. FIG. 7D is a graph showing the inner product value |Pr| against degree in the middle-flow region.

Shown in FIG. 7A is the inner product value |Pr| against degree of sampling points in the noise region of system noise (random noise) which appears in a part deep inside the object in the C-mode image. The inner product value |Pr| for 0 degree (where degree is 0) is smaller in the noise region than in other regions. Shown in FIG. 7B is the inner product value |Pr| against degree of each sampling point in the clutter region which corresponds to the tissue part in the C-mode image. The inner product value |Pr| for 0 degree is larger in the clutter region than in the noise region.

Shown in FIG. 7C is the inner product value |Pr| against degree of sampling points in the high-flow region which has abundant blood flow (where blood flow is fast) in the C-mode image. The inner product value |Pr| for middle to high degrees is larger in the high-flow region than in other regions. Shown in FIG. 7D is the inner product value |Pr| against degree of sampling points in the middle-flow region which has weaker blood flow (where blood flow is slow) than the high-flow region in the C-mode image. The inner product value |Pr| for middle to high degrees is a bit larger in the middle-flow region than in the noise and clutter regions.

An object of the MTI filter 73 is to remove signals in the clutter region (and the noise region). To that end, the removal rate Rf for each degree is determined, defining the solid lines in FIGS. 7A to 7D as threshold values, for example.

Figure 8A:
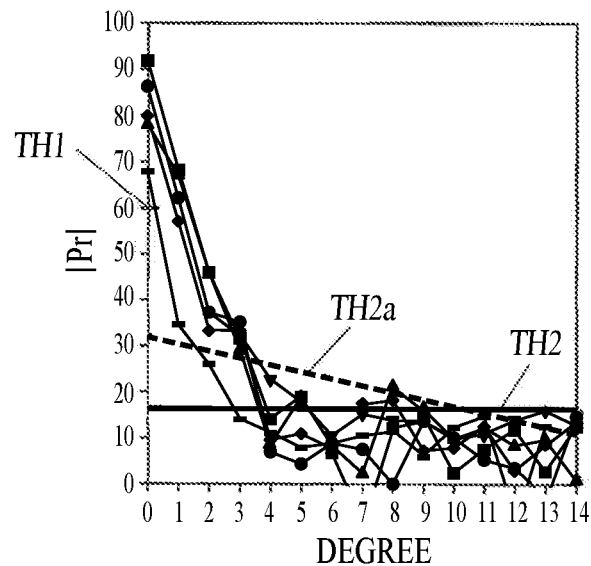
FIG. 8A is a graph showing the inner product value against degree of a sampling point in the clutter region in a C-mode image with a first threshold value and a second threshold value.
Figure 8B:
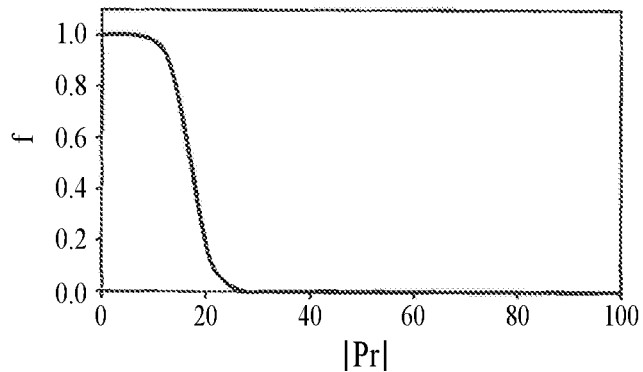
FIG. 8B is a graph showing the gain of a first removal rate conversion function against inner product value independent of degree.
Figure 8C:
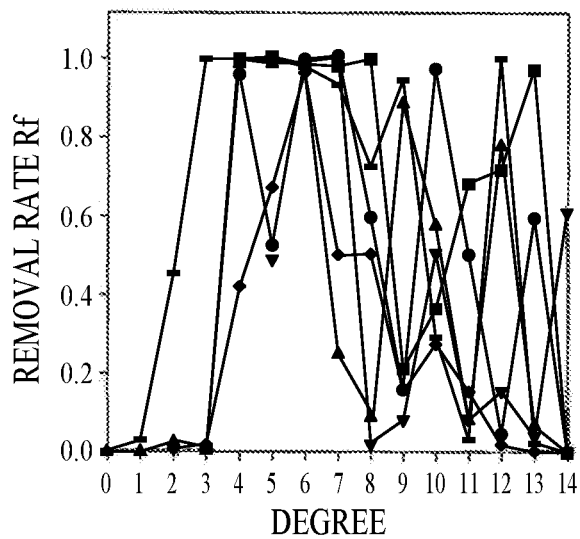
FIG. 8C is a graph showing a removal rate against degree when a first removal rate conversion function is used.
Figure 9A:
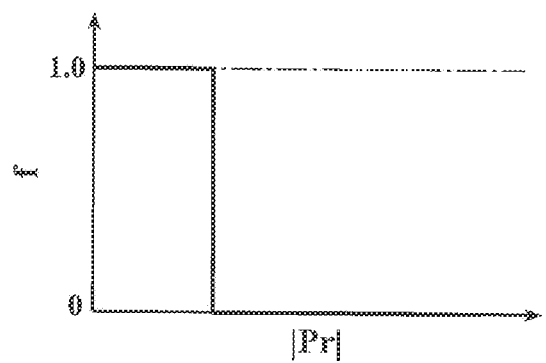
FIG. 9A is a graph showing the gain of the first removal rate conversion function which is a step function to the inner product value.
Figure 9B:
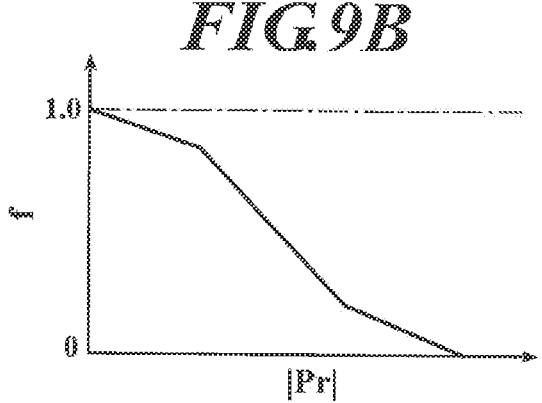
FIG. 9B is a graph showing the gain of the first removal rate conversion function which is a sigmoid function to the inner product value.
Figure 10:
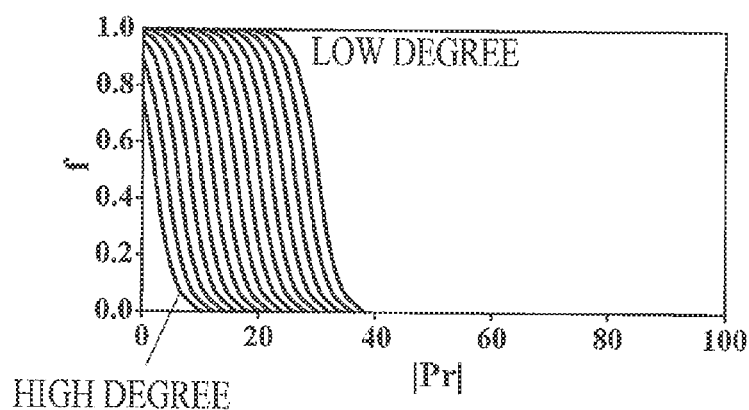
FIG. 10 is a graph showing the gain of the first removal rate conversion function against inner product value different for each degree.

Next, the calculation of the removal rate is described with reference to FIGS. 8A to 10. FIG. 8A is a graph showing the inner product value |Pr| against degree of sampling points in the clutter region in the C-mode image with a threshold value TH1 and a second threshold values TH2 and T2a. FIG. 8B is a graph showing the gain of a first removal rate conversion function f against inner product value |Pr| independent of degree. FIG. 8C is a graph showing the removal rate Rf against degree when the removal rate conversion function f is used. FIG. 9A is a graph showing the gain of the removal rate conversion function f which is a step function to the inner product value |Pr|. FIG. 9B is a graph showing the gain of the removal rate conversion function f which is a sigmoid function to the inner product value |Pr|. FIG. 10 is a graph showing the gain of the removal rate conversion function f against inner product value |Pr| different for each degree.

As shown in FIG. 8A, when the inner product value |Pr| for each degree in the clutter region is obtained, the first threshold value TH1 and the second threshold value TH2 as evaluation criteria data are set. The first threshold value TH1 is a threshold value for determining the inner product value |Pr| for 0 degree in the noise region. Accordingly, the sampling points whose inner product value |Pr| for 0 degree is equal to or lower than the first threshold value TH1 are assumed to be the noise region and are to be removed for all degrees.

The second threshold value TH2 is a threshold value for determining the inner product value |Pr| in the clutter region.

Accordingly, degree for which the inner product value |Pr| is equal to or less than the second threshold value TH2 is assumed to be the clutter region and removed. The removal rate conversion function f of the gain against inner product value |Pr| shown in FIG. 8B is determined corresponding to the second threshold value TH2. The gain of the removal rate conversion function f is determined in a range from 0 to 1. When the gain of the removal rate conversion function f=0, the removal rate is 0%, and when the gain of the removal rate conversion function f=1, the removal rate is 100%.

The removal rate conversion function f may be a step function as shown in FIG. 9A or a sigmoid function as shown in FIG. 9B. A monotone decreasing function is desirable for the removal rate conversion function f, where the removal rate can be set higher as the inner product value Pr is smaller.

The removal rate Rf against degree shown in FIG. 8C is calculated by converting the inner product value |Pr| of the sampling points in FIG. 8A with the removal rate conversion function f in FIG. 8B. The sampling points whose inner product value |Pr| for 0 degree is equal to or lower than the first threshold value TH1, the removal rate for all degrees is set to 1.

As shown in FIG. 8A, instead of the second threshold value TH2 which is constant and common to all degrees, the second threshold value TH2a which varies by degree may be set. The removal rate conversion function f of the gain against the inner product value |Pr| for each degree shown in FIG. 10 is determined corresponding to the second threshold value TH2a. The removal rate conversion function f in FIG. 10 varies from low degrees to high degrees.

Returning to FIG. 3, the inner product value calculating section 731 reads out the orthonormal basis $b^H$ from the orthogonal basis storage 732 under the control of the control section 9, and calculates the inner product value Pr for each degree k (k=0, 1, . . . , n−1) of each sampling point (pixel) in one frame by the formula (3A) using the packet data Sp (Doppler signals I and Q) input from the corner-turn control section 72 and the orthonormal basis $b^H$. The orthogonal basis storage 732 is a storage which stores the orthonormal bases b and $b^H$ which are predetermined.

The evaluation criteria data storage 733 is a storage which stores the first threshold value and the removal rate conversion function f based on the second threshold value which are predetermined as the evaluation criteria data. The evaluation criteria data storage 733 may be configured to suitably modify the data to be stored according to the input by the operator via the control section 2.

The conversion function setting section 734 reads out the first threshold value and the removal rate conversion function f based on the second threshold value from the evaluation criteria data storage 733 under the control of the control section 9, and generates the removal rate conversion function f to convert the removal rate into 1 for all degrees when the inner product value |Pr| (the absolute value of the inner product Pr) input from the inner product value calculating section 731 for 0 degree is equal to or lower than the first threshold value. The conversion function setting section 734 sets the removal rate conversion function f read out when the inner product value |Pr| for 0 degree is higher than the first threshold value.

The removal rate calculating section 735 calculates the removal rate Rf for each degree by converting the inner product value |Pr| input from the inner product value calculating section 731 by the removal rate function f input from the conversion function setting section 734, under the control of the control section 9.

The filtering section 736 reads out the orthonormal basis $b^H$ from the orthogonal basis storage 732 under the control of the control section 9, and calculates the packet data $Sp_{MTIed}$ by the formula (3), using the orthonormal basis $b^H$ read out, the removal rate Rf input from the removal rate calculating section 735, and the inner product value Pr input from the inner product value calculating section 731. The filtering section 736 separates the packet data $Sp_{MTIed}$ as a complex Doppler signal to Doppler signals I and Q, and outputs them to the correlation calculating section 74.

Returning to FIG. 2, the correlation calculating section 74 calculates the real part D and the imaginary part N of the average value S of the autocorrelation of the Doppler signal (the average value of phase difference vector) by the following formula (5) from the Doppler signals I and Q (a complex Doppler signal z) filtered by the MTI filter 73, under the control of the control section 9.

[Mathematical Formula 1]

$$S = \sum_{k=0}^{n-1} z_k^* \cdot z_{k+1} = D + jN \quad (5)$$

The data converting section 75 calculates the blood flow velocity V, the power P, and the variance T from the Doppler signals I and Q filtered by the MTI filter 73, and the real part D and the imaginary part N of the average value S of the autocorrelation of the Doppler signal, under the control of the control section 9. To be more concrete, the data converting section 75 calculates the blood flow velocity V from the real part D and the imaginary part N of the average value S of the autocorrelation of the Doppler signal by the following formula (6).

[Mathematical Formula 2]

$$V = \tan^{-1}\frac{N}{D} \quad (6)$$

The data converting section 75 calculates the power P as the average value of the intensity of the Doppler signal from the Doppler signals I and Q (the complex Doppler signal z) by the following formula (7).

[Mathematical Formula 3]

$$P = \frac{1}{n}\sum_{k=0}^{n-1}|z_k|^2 \quad (7)$$

The data converting section 75 also calculates the variance T as the ratio of the magnitude of phase difference vector and the power (subtracted from 1 to switch magnitude) from the Doppler signals I and Q (the complex Doppler signal z) by the following formula (8).

[Mathematical Formula 4]

$$T = 1 - \frac{\sqrt{D^2 + N^2}}{P} \quad (8)$$

The noise removal spatial filter section 76 filters the power P, the blood flow velocity V and the variance T calculated by the data converting section 75. The noise removal spatial filter section 76 has a key hole filter and a spatial filter (not shown in the drawings).

The key hole filter removes noise by filtering the power P, the blood flow velocity V and the variance T which are the parameters of each frame of the C-mode image. In V-mode and V-T mode, the key hole filter filters the blood flow velocity V by removing the blood flow velocity V in the region to be removed decided by the blood flow velocity V and the power P calculated by the data converting section 75. In V mode and V-T mode, the blood flow velocity V is used for the image displaying (coloring). In P mode, the key hole filter filters the power P by removing the power P in the region to be removed decided by the blood flow velocity V and the power P calculated by the data converting section 75. In P mode, the power P is used for image displaying (coloring).

To be more concrete, in V mode and V-T mode, the key hole filter regards the blood flow signal in the region where the blood flow velocity V is lower than a predetermined threshold value as a clutter noise and the blood flow signal where the power P is lower than a predetermined threshold value as a background noise, and removes the velocity V in these regions. In P mode, the key hole filter regards the blood flow signal in the region where the blood flow velocity V is lower than a predetermined threshold value as a clutter noise and the blood flow signal where the power P is lower than a predetermined threshold value as a background noise, and remove the power P in these regions.

The spatial filter is a two-dimensional weighted average filter for smoothing the data of the blood flow velocity V, the power P, and the variance T which are parameters of each frame of the C-mode image. In V mode and V-T mode, the spatial filter filters the blood flow velocity V filtered by the key hole filter and the variance T calculated by the data converting section 75. In P mode, the spatial filter filters the power P filtered by the key hole filter.

The inter-frame filter 77 filters to smooth the unevenness between frames and keeps a residual image in the blood flow components in each frame which are the parameters of the C-mode image among the blood flow velocity V, the power P, and the variance T filtered by the noise removal spatial filter section 76, corresponding to a display mode input from the operating section 2.

The C-mode image converting section 78 generates the C-mode image data by converting the blood flow velocity V, the power P and the variance T filtered by the inter-frame filter 77.

Returning to FIG. 1, the display processing section 8 executes a process to construct display image data to be displayed on the display 12 and display the display image data on the display 12. Especially when the B-mode is selected, it executes a process where the B-mode image of the B-mode image data generated in the B-mode image generating section 5 gets included in the display image data as an ultrasound image. When the C-mode is selected, it executes a process of generating the combined image data, as an ultrasound image, in which the C-mode image of C-mode image data generated in C-mode image generating section 7 is superimposed at the point of ROI selected in the B-mode image generated in the B-mode image generating section 5 and including it in the display image data.

The control section 9, for example, is configured by including a central processing unit (CPU), a read only memory (ROM), and a random access memory (RAM), reads out and expands to the RAM a variety of processing programs such as a system program stored in the ROM, and controls the operation of each part of the ultrasound diagnostic device 1 according to the program expanded. The RAM forms a work area which temporally stores the programs executed by the CPU and the data concerned. The ROM includes a nonvolatile memory, such as a semiconductor and so forth, and stores the system program of the ultrasound diagnostic device 1, other processing programs such as an initial setting program and an ultrasound diagnosis program which can be executed in the system program and various data. These programs are stored in a form of program codes which can be read by the computer and the CPU executes successively the operations according to the program codes concerned.

The storage 11 incorporates large capacity storage media such as a hard disk drive (HDD) and stores the ultrasound image data (B-mode image data, C-mode image data, combined image data) and so forth.

The display 12 is what is called a monitor such as a liquid crystal display (LCD), an electroluminescence (EL) display to display the image data output from the display processing section 8.

Part or all of any of the functions in each functional block of the elements incorporated to the ultrasound diagnostic device 1 can be effectuated as a hardware circuit like an integrated circuit. An integrated circuit is an LSI (large-scale integration), for example. The LSI is classified as system LSI, super LSI (super-large-scale integration), ULSI (ultra-large-scale integration), or just IC (integrated circuit), according to degree of integration. The method of integrated circuit formation is not limited to LSI, but may be realized by a dedicated circuit or a general-purpose processor, and a field programmable gate array (FPGA) or a reconfigurable processor which allows reconfigurations of connection and setting of circuit cells inside LSI. Part or all of any of the functions in each functional block of the elements incorporated to the ultrasound diagnostic device 1 can be effectuated by software. In this case, the software is installed in one or more of storage media such as ROMs, optical discs or hard disks and is executed by an operation processor.

Next, the MTI filter 73 of the ultrasound diagnostic device 1 in the present embodiment is described with reference to FIG. 11. FIG. 11 is a flow chart showing the process of the first MTI filtering.

The MTI filter 73 executes the process of the first MTI filtering with each section of the MTI filter 73 under the control of the control section 9. The explanation on the control by the control section 9 is omitted.

In the process of the first MTI filtering, the inner product value calculating section 731 first obtains the packet data Sp (xc, yc, i) from the corner-turn control section 72 (step S31), as shown in FIG. 11. Here xc and yc of (xc, yx, i) denote the spatial location (two dimensional coordinates) in one frame in the C-mode image, and i denotes the degree (0, 1, ..., n−1) of the orthonormal basis b.

The inner product value calculating section 731 reads out the orthonormal basis $b^H$ from the orthogonal basis storage 732 and calculates the inner product value Pr (xc, yc, i) of the degree i by the formula (3A) using the packet data Sp (xc, yc, i) obtained in the step S11 and the orthonormal basis $b^H$ (Step S12). In the step S12, the inner product value Pr (xc, yc, i) for every degree i is calculated, for example.

The conversion function setting section 734 then reads out the removal rate conversion function f (Pr, i) based on the first and second threshold values as the evaluation criteria data from the evaluation criteria data storage 733 (Step S13). As to the inner product value |Pr (xc, yc, i)| calculated in the step S12, the conversion function setting section 734 sets the removal rate conversion function f (Pr, i) to fix the removal rates for all degrees to 1 when the inner product value |Pr (xc, yc, i)| for 0 degree is equal to or lower than the first threshold value, and sets the removal rate conversion function f (Pr, i) read out in the step S13, when the inner product value |Pr| is higher than the first threshold value (Step S14).

The removal rate calculating section 735 calculates the removal rate Rf (xc, yc, i) for each degree by converting the inner product value Pr (xc, yc, i) calculated in the step S12 using the removal rate conversion function f (Pr, i) set in the step S14 (Step 15).

The filtering section 736 multiplies the inner product value Pr (xc, yc, i) calculated in the step S12 by the removal rate Rf (xc, yc, i) calculated in the step S15 (Step S16). And the filtering section 736 reads out the orthonormal basis b from the orthogonal basis storage 732 and calculates the removal data (term obtained by removing I from the right side of the formula (3) and inverting sign) using the inner product value Pr (xc, yc, i) multiplied by the removal rate Rf (xc, yc, i) in the step S16 and the orthonormal basis b read out (Step S17). Next, the filtering section 736 calculates the packet data $Sp_{MTIed}$ (xc, yc) in the formula (3) by subtracting the removal data calculated in the step S17 from the packet data Sp (xc, yc, i) obtained in the step S11, separates the packet data $Sp_{MTIed}$ (xc, yc) to Doppler signals I and Q, outputs them to the correlation calculating section 74 (Step S18) and ends the process of the first MTI filtering. The process of the first MTI filtering of one frame in the C-mode image is repeatedly applied to every sampling point of spatial location in the frame.

In accordance with the present embodiment described hereinbefore, an ultrasound diagnostic device 1 has a transmitter 3 which outputs a driving signal for the C-mode image to a ultrasound probe 101 sending and receiving ultrasound, a receiver 4 which obtains a reception signal from the ultrasound probe 101, an inner product value calculating section 731 which calculates an inner product value Pr for each degree of packet data of the reception signal and an orthonormal basis $b^H$, a conversion function setting section 734 which sets a removal rate conversion function f to convert the inner product value Pr into a removal rate Rf to remove clutter components, a removal rate calculating section 735 which converts the calculated inner product value Pr into a removal rate Rf for each degree by using the set removal rate conversion function f, and a display processing section 8 which generates a combined image data from which signal components of the C-mode image are removed according to the removal rate Rf for each degree.

The inner product value indicates the approximate characteristics of blood flow, clutter, and noise in the packet data. The magnitude of the inner product corresponds to the intensity (power) of the orthonormal basis components. The clutter has a high power and a low velocity and the blood flow has a low power and a high velocity. Therefore, the inner product value is useful as information for evaluation. It can optimize S/N, as the characteristics of the MTI filtering for the packet data can be suitably modified. The blurring caused by smoothing can be reduced as the noise removal intensity is adjusted according to the possibility of noise (removal rate).

Further, the system noise (random noise) can be effectively removed as well as the clutter by using the inner product value.

The conversion function setting section 734 sets the removal rate conversion function f to convert the removal rate for all degrees into 1 when the inner product value Pr for 0 degree calculated is equal to or lower than the predetermined first threshold value. Thus, the system noise can be removed more effectively.

The display processing section 8 displays the combined image data from which the signal components of the C-mode image are removed according to the removal rate Rf for each degree on the display 12. Thus the examiner can observe the C-mode image whose S/N of the blood flow signal is optimized.

The ultrasound diagnostic device 1 has a filtering section 736 to calculate the filtered packet data, in which the calculated inner product value Pr for each degree is multiplied by the removal rate Rf for each degree, the inner product value Pr multiplied by the removal rate Rf for each degree is multiplied by the orthonormal basis b (Hermitian transposed matrix of the orthonormal basis $b^H$), and the value multiplied by the orthonormal basis b is subtracted from the packet data, and a C-mode image converting section 78 to generate C-mode image data from the filtered packet data. The display processing section 8 displays the C-mode image of the C-mode image data after the filtering on the display 12. This makes it possible to obtain easily and accurately the packet data obtained by removing the signal components of C-mode image from the original packet data according to the removal rate.

The removal rate Rf for each degree ranges from 0 to 1. Because of this, in comparison to the conventional art in which RankCut components are valued either 0 or 1, the stability improves as the removal rate ranging from 0 to 1 reflects ambiguities of the data.

First Modification Example

The first modification example of the first embodiment described above is described with reference to FIGS. 12 to

14. First, the device structure of the present modification example is described with reference to FIGS. 12 to 13C. FIG. 12 is a block diagram showing the functional structure of the MTI filter 73A.

The ultrasound diagnostic device 1 in the first embodiment described above is used as the device structure of the present modification example. However, the MTI filter 73 is substituted by the MTI filter 73A shown in FIG. 12. The explanation is, therefore, focused on the elements different from the first embodiment. The same elements share the numbering in the drawings, and their descriptions are omitted.

As shown in FIG. 12, the MTI filter 73A has an inner product value calculating section 731, an orthogonal basis storage 732, an inner product difference value calculating section 737 as an inner product difference value obtaining section, an evaluation criteria data storage 733A, a conversion function setting section 734A, a removal rate calculating section 735A as a removal rate obtaining section and a filtering section 736.

The inner product value calculating section 731 calculates the inner product value Pr for each degree k (k=0, 1, . . . , n−1) of each sampling point in one frame of the C-mode image, but the inner product value Pr in the one frame concerned is calculated, for example.

The inner product difference value calculating section 737 calculates an inner product difference value dPr of each sampling point in one frame by the following formula (9) using the inner product value Pr for one frame input from the inner product value calculating section 731 under the control of the control section 9.

$$dPr = Pr \text{ of a center point} - (\text{the average of inner product values in the surrounding region}) \quad (9)$$

center point: sampling point (1 pixel)
surrounding region: 8 pixels surrounding the center point The surrounding region is not limited to this specification and it can be set as a region of actual size (*mm×*mm) surrounding the center point. The value to be subtracted from the Pr of the center point is not limited to (the average inner product value in the surrounding region) and it can be the median of the inner product values in the surrounding region, for example.

Figure 13A:
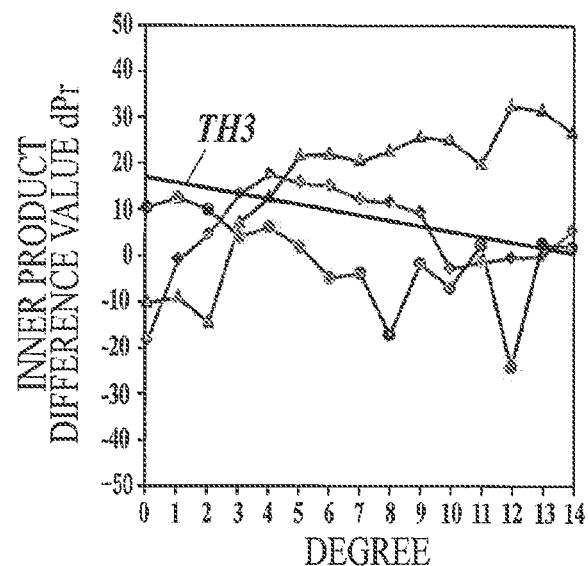
FIG. 13A is a graph showing inner product difference values against degree in the clutter region, the middle flow region and the high flow region.
Figure 13B:
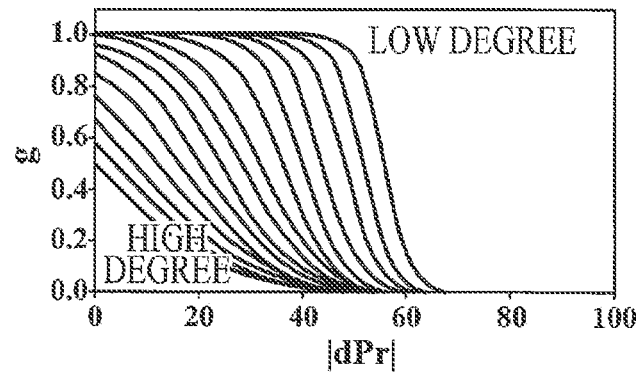
FIG. 13B is a graph showing the gain for each degree of the second removal rate conversion function against inner product difference value.
Figure 13C:
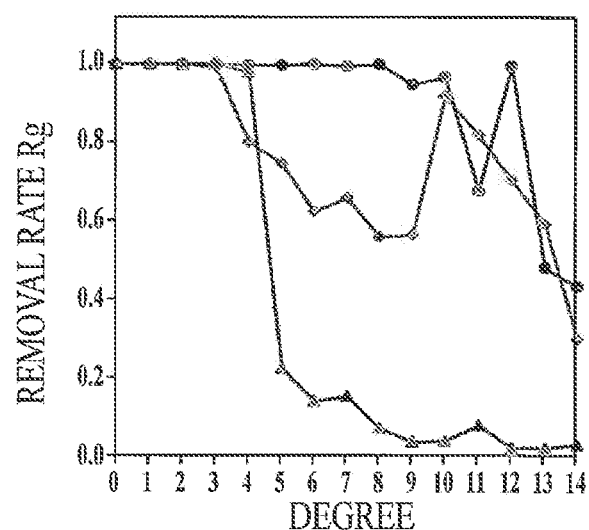
FIG. 13C is a graph showing removal rates against degree when the second removal rate conversion function is used.

Explained hereinafter is the calculation of the removal rate using the inner product difference value dPr with reference to FIGS. 13A to 13C. FIG. 13A is a graph showing the inner product difference values dPr against degree in the clutter region, the middle flow region and the high flow region. FIG. 13B is a graph showing the gain of the second removal rate conversion function g for inner product difference value |dPr| different for each degree. FIG. 13C is a graph showing the removal rate Rg against degree when the removal rate conversion function g is used.

As shown in FIG. 13A, the third threshold value TH3 is set when the inner product difference values dPr for each degree in the clutter region, the middle flow region, and the high flow region are obtained. The inner product difference value dPr in the clutter region is plotted with circle marks, the inner product difference value dPr in the middle flow region with square marks, and the inner product difference value dPr in the high flow region with triangle marks.

The third threshold value TH3 is a threshold value for determining the inner product difference value dPr in the clutter region. Accordingly, degree for which the inner product difference value dPr is equal to or lower than the third threshold value TH3 is assumed to be the clutter region and removed. The removal rate conversion function g of the gain against the inner product difference value |dPr| (the absolute value of the inner product difference value) different for each degree shown in FIG. 13B is determined corresponding to the third threshold TH3. The gain of the removal rate conversion function g is determined in a range from 0 to 1. When the gain of the removal rate conversion function g=0, the removal rate is 0%, and when the gain of the removal rate conversion function g=1, the removal rate is 100%.

The removal rate conversion function g may be a step function as shown in FIG. 9A or a sigmoid function as shown in FIG. 9B, like the removal rate conversion function f. A monotone decreasing function is desirable for the removal rate conversion function g.

The removal rate Rg against degree shown in FIG. 13C is calculated by converting the inner product difference value dPr of the sampling point in FIG. 13A with the removal rate conversion function g in FIG. 13B. Instead of the second threshold value TH2 which varies by degree, the removal rate conversion function g common to all degrees can be set according to the third threshold value which is constant and common to all degrees.

Returning to FIG. 12, the evaluation criteria data storage 733A is a storage which stores the removal rate conversion function g according to the third threshold value, which is predetermined. The evaluation criteria data storage 733A may be configured to suitably modify the data to be stored according to the input by the operator via the control section 2.

The conversion function setting section 734A reads out the removal rate conversion function g based on the third threshold value from the evaluation criteria data storage 733 under the control of the control section 9, and sets the read out removal rate conversion function g.

The removal rate calculating section 735A calculates the removal rate Rg for each degree by converting the inner product difference value dPr input from the inner product difference value calculating section 737 using the removal rate function g input from the conversion function setting section 734A, under the control of the control section 9.

The filtering section 736 reads out the orthonormal basis b from the orthogonal basis storage 732 under the control of the control section 9, and calculates the packet data $Sp_{MTIed}$ by the formula (3), using the orthonormal basis b read out, the removal rate Rg input from the removal rate calculating section 735A, and the inner product value Pr input from the inner product value calculating section 731. The filtering section 736 separates the packet data $Sp_{MTIed}$ as a complex Doppler signal to Doppler signals I and Q, and outputs them to the correlation calculating section 74.

Next, the MTI filter 73A of the ultrasound diagnostic device 1 in the present modification example is described with reference to FIG. 14. FIG. 14 is a flow chart showing the process of the second MTI filtering.

The MTI filter 73A executes the process of the second MTI filtering with each section of the MTI filter 73A under the control of the control section 9. The explanation on the control by the control section 9 is omitted.

As shown in FIG. 14, the steps S21 and S22 in the process of the second MTI filtering are the same as the steps S11 and S12 in the process of the first MTI filtering in FIG. 11. In the step S22, the inner product value Pr (xc, yc, i) of one frame in the C-mode image is calculated.

The inner product difference value calculating section 737 calculates the inner product difference value dPr (xc, yc, i) by the formula (9) using the inner product value Pr (xc, yc, i) of one frame obtained in the step S32 (Step S23). The conversion function setting section 734A reads out the removal rate conversion function g (dPr, i) based on the third threshold value as the evaluation criteria data from the evaluation criteria data storage 733A (Step S24). The conversion function setting section 734 sets the removal rate conversion function g (dPr, i) read out in the step S24 (Step S25).

The removal rate calculating section 735A calculates the removal rate Rg (xc, yc, i) for each degree by converting the inner product difference value dPr (xc, yc, i) calculated in the step S23 using the removal rate conversion function g (dPr, i) set in the step S25 (Step S26). The filtering section 736 multiplies the inner product value Pr (xc, yc, i) calculated in the step S22 by the removal rate Rg (xc, yc, i) calculated in the step S26 (Step S27).

The steps S28 and S29 are the same as S17 and S18 in the process of the first MTI filtering in FIG. 11.

In accordance with the present modification example described hereinbefore, the ultrasound diagnostic device 1 has an inner product difference value calculating section 737 which calculates an inner product difference value dPr for each degree between an inner product value of a center point in the C-mode image for each degree and an inner product value of a region surrounding the center point concerned for each degree. The conversion function setting section 734A sets the removal rate conversion function g to convert the inner product difference value dPr into the removal rate Rg to remove the clutter components. The removal rate calculating section 735A converts the calculated inner product difference value dPr into the removal rate Rg for each degree by the removal rate conversion function g.

The clutter components tend to be global and the blood flow components tend to be local. By calculating the inner product difference value, it is possible to differentiate the clutter which is global information and the blood flow which is local information. This makes it possible to remove the clutter more effectively by differentiating the blood flow components from the other components by comparison with the surrounding region.

Second Modification Example

Figure 15:
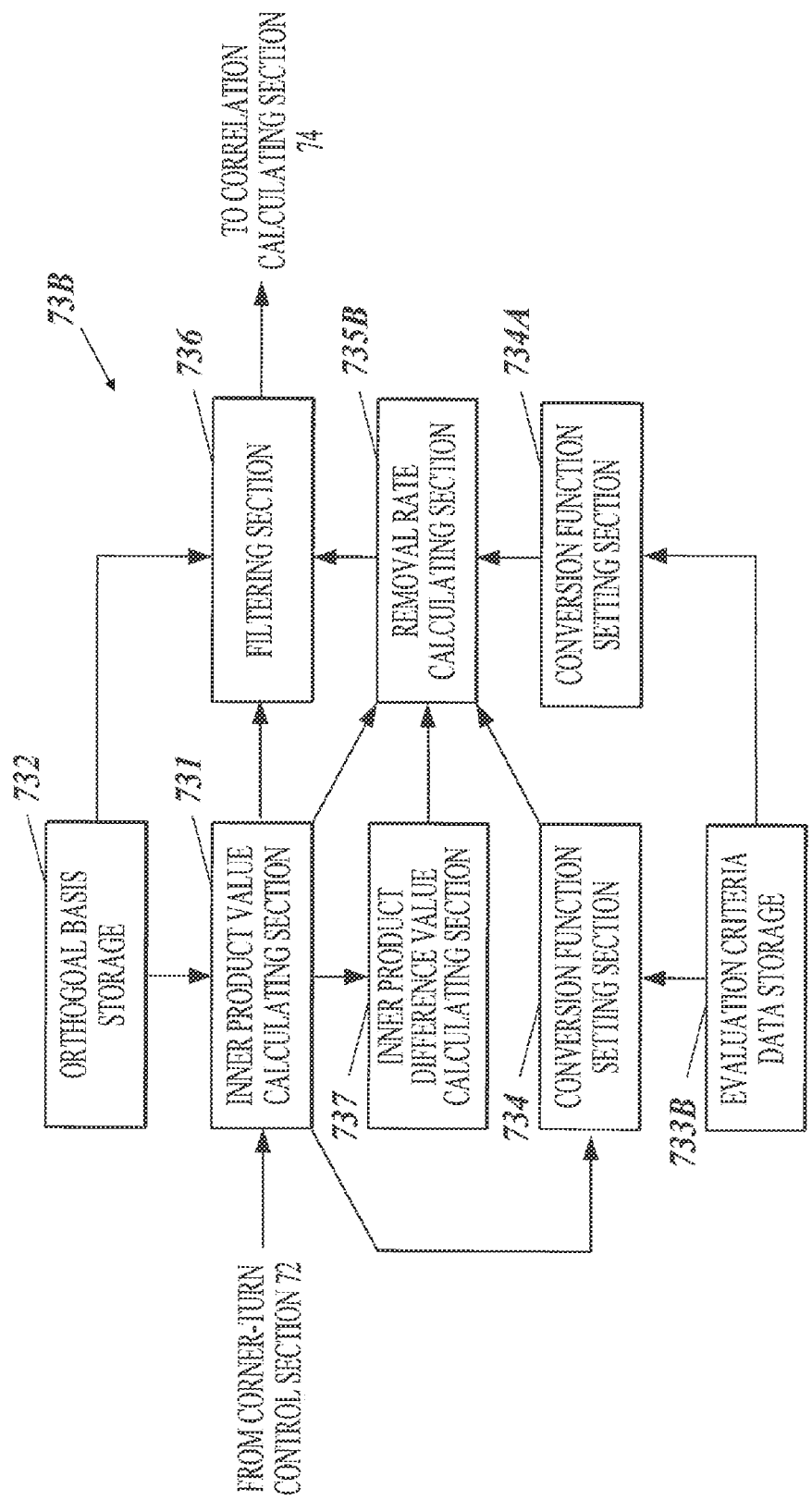
FIG. 15 is a block diagram showing the functional structure of a third MTI filter.
Figure 16:
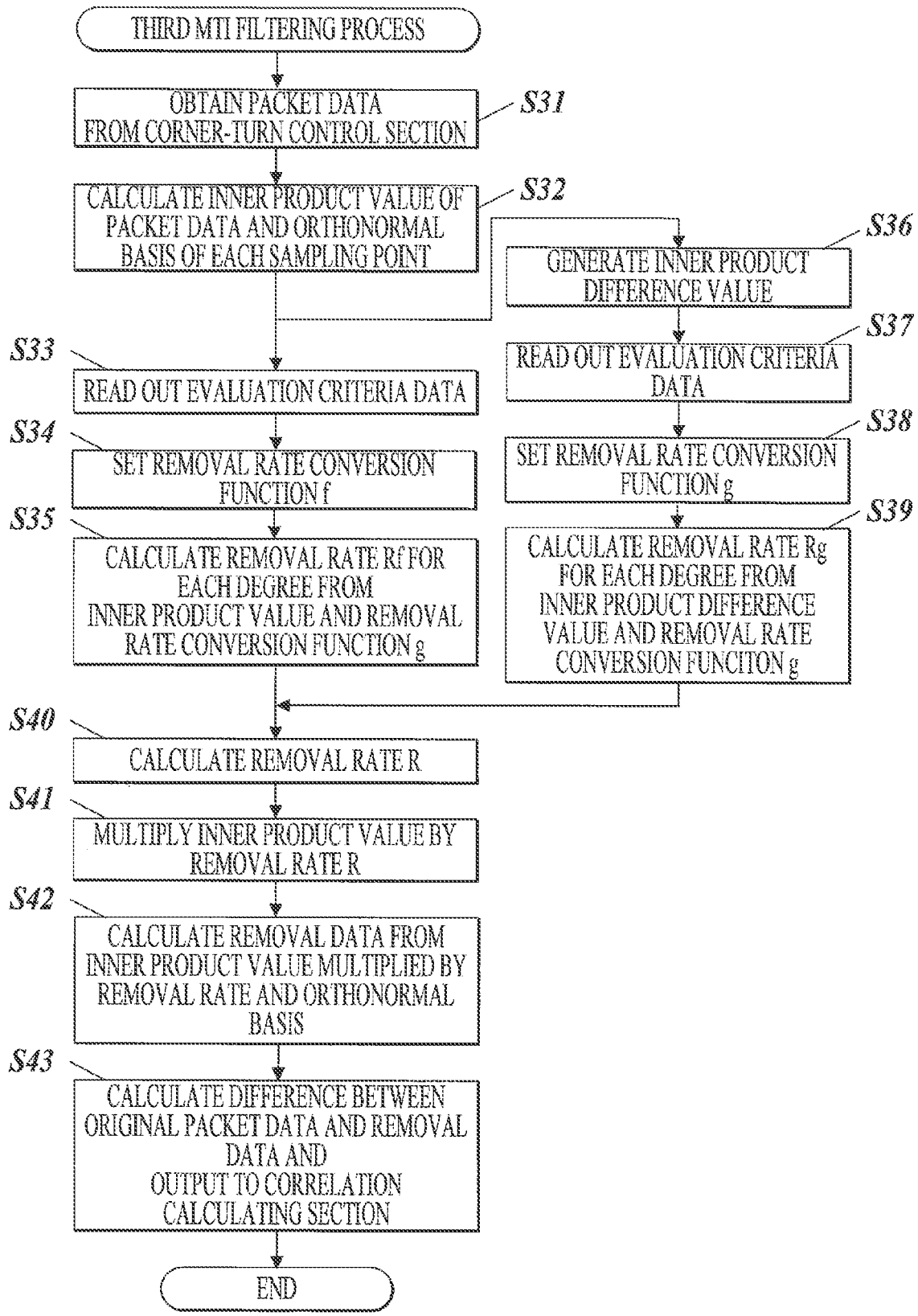
FIG. 16 is a flow chart showing the process of third MTI filtering.

With reference to FIGS. 15 and 16, the second modification example of the first embodiment described above is explained. The device structure of the present modification example is explained with reference to FIG. 15. FIG. 15 is a block diagram showing the functional structure of the MTI filter 73B.

The ultrasound diagnostic device 1 in the first embodiment described above is used as the device structure of the present modification example. However, the MTI filter 73 is substituted by the MTI filter 73B shown in FIG. 15. The explanation is, therefore, focused on the elements different from the first embodiment and its first modification example. The same elements share the numbering in the drawings, and their descriptions are omitted.

As shown in FIG. 15, the MTI filter 73A has an inner product value calculating section 731, an orthogonal basis storage 732, an inner product difference value calculating section 737, an evaluation criteria data storage 733B, a conversion function setting section 734, a conversion function setting section 734A, a removal rate calculating section 735B as a removal rate obtaining section, and a filtering section 736.

The inner product value calculating section 731 calculates the inner product value Pr for each degree k (k=0, 1, ..., n−1) of each sampling point (pixel) in one frame of the C-mode image, but the inner product value Pr in the one frame concerned is calculated, for example.

The evaluation criteria data storage 733B is a storage which stores the first threshold value, the removal rate conversion function f based on the second threshold value, and the removal rate conversion function g based on the third threshold value which are predetermined. The evaluation criteria data storage 733B may be configured to suitably modify the data to be stored according to the input by the operator via the control section 2.

Under the control by the control section 9, the removal rate calculating section 735B calculates the removal rate Rf for each degree by converting the inner product value |Pr| input from the inner product value calculating section 731 using the removal rate conversion function f input from the conversion function setting section 734, and calculates the removal rate Rg for each degree by converting the inner product difference value dPr input from the inner product difference value calculating section 737 using the removal rate conversion function g input from the conversion function setting section 734A. The removal rate calculating section 735B calculates the removal rate R with the calculated removal rates Rf and Rg. The removal rate R is, for example, the average value or maximum value of the removal rates Rf and Rg. The maximum value of the removal rates Rf and Rg is supposed to be relatively effective.

The filtering section 736 reads out the orthonormal basis b from the orthogonal basis storage 732 under the control of the control section 9, and calculates the packet data $Sp_{MTIed}$ by the formula (3), using the orthonormal basis b read out, the removal rate R input from the removal rate calculating section 735B, and the inner product value Pr input from the inner product value calculating section 731. The filtering section 736 separates the packet data $Sp_{MTIed}$ as a complex Doppler signal to Doppler signals I and Q, and outputs them to the correlation calculating section 74.

Next, the MTI filter 73B of the ultrasound diagnostic device 1 in the present modification example is explained with reference to FIG. 16. FIG. 16 is a flow chart showing the process of the third MTI filtering.

The MTI filter 73B executes the process of the third MTI filtering with each section of the MTI filter 73B under the control of the control section 9. The explanation on the control by the control section 9 is omitted.

As shown in FIG. 16, the steps S31 to S35 in the process of the third MTI filtering are the same as the steps S11 to S15 in the process of the first MTI filtering in FIG. 11. In the step S32, the inner product value Pr (xc, yc, i) of one frame in the C-mode image is calculated. The steps S36 to S39 are the same as S23 to S26 in the process of the second MTI filtering in FIG. 14. The steps S35 and S39 are mainly executed by the removal rate calculating section 735B.

The removal rate calculating section 735B calculates the removal rate R (xc, yc, i) by taking the maximum value or average value of the removal rate Rf (xc, yc, i) calculated in the step S35 and the removal rate Rg (xc, yc, i) calculated in the step S39 (Step S40). The filtering section 736 multiplies the inner product value Pr (xc, yc, i) calculated in the step S32 by the removal rate R (xc, yc, i) calculated in the step S40 (Step S41).

The steps S42 and S43 are the same as S17 and S18 in the process of the first MTI filtering in FIG. 11.

In accordance with the present modification example described hereinbefore, the conversion function setting sections 734 and 734A set the removal rate conversion function f to convert the inner product value Pr into the removal rate Rf to remove the clutter components, and set the removal rate conversion function g to convert the inner product difference value dPr into the removal rate Rg to remove the clutter components. The removal rate calculating section 735B converts the calculated inner product value Pr for each degree into the removal rate Rf for each degree using the removal rate conversion function f, converts then the calculated inner product difference value dPr for each degree to the removal rate Rg for each degree using the removal rate conversion function g, and calculates the removal rate R with the removal rates Rf and Rg. Thus, the system noise can be effectively removed with the inner product value, and the clutter can also be effectively removed with the inner product difference value.

The removal rate calculating section 735B sets the removal rate R for each degree to the maximum of the removal rate Rf for each degree and the removal rate Rg for each degree. This allows effective removal of the system noise and clutter.

Second Embodiment

Figure 17:
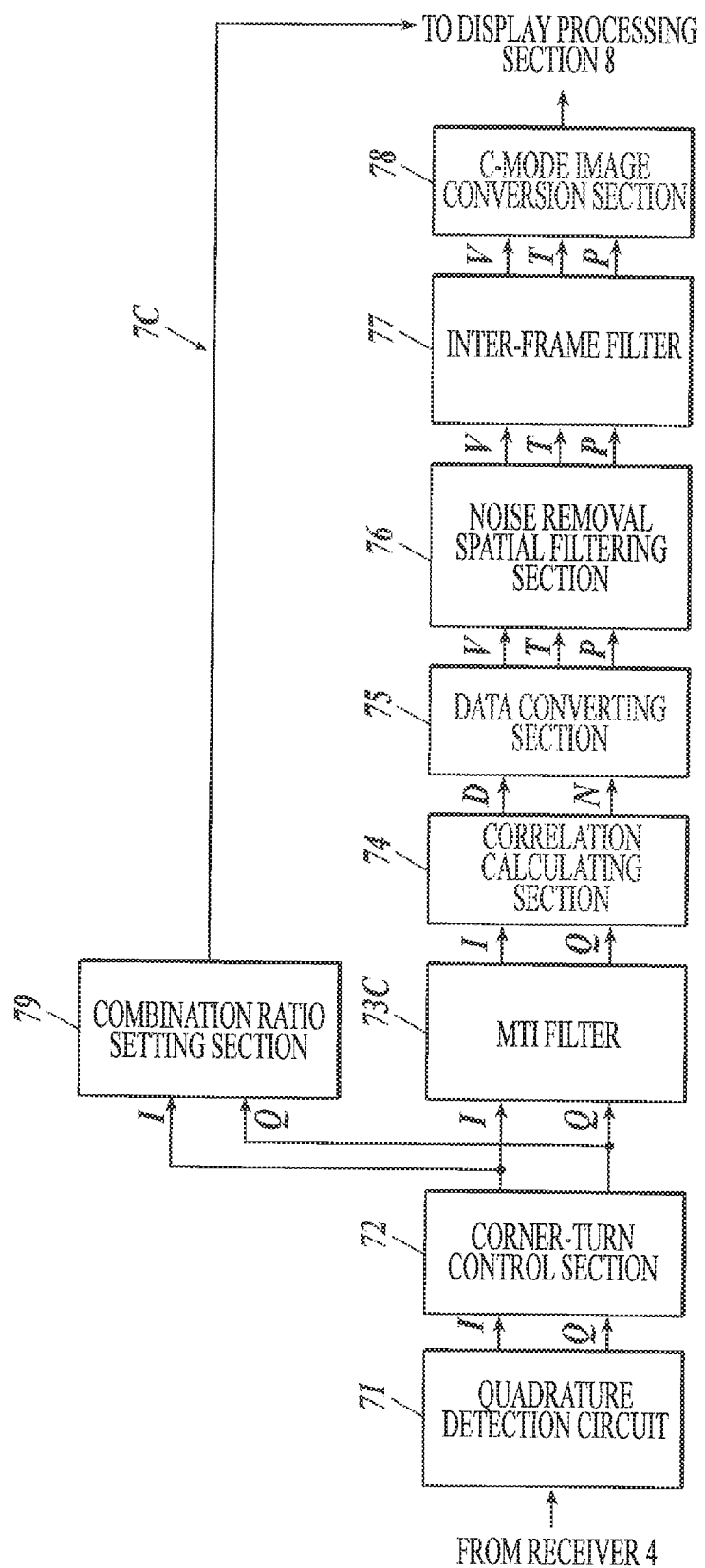
FIG. 17 is a block diagram showing the functional structure of a second C-mode image generating section.
Figure 18:
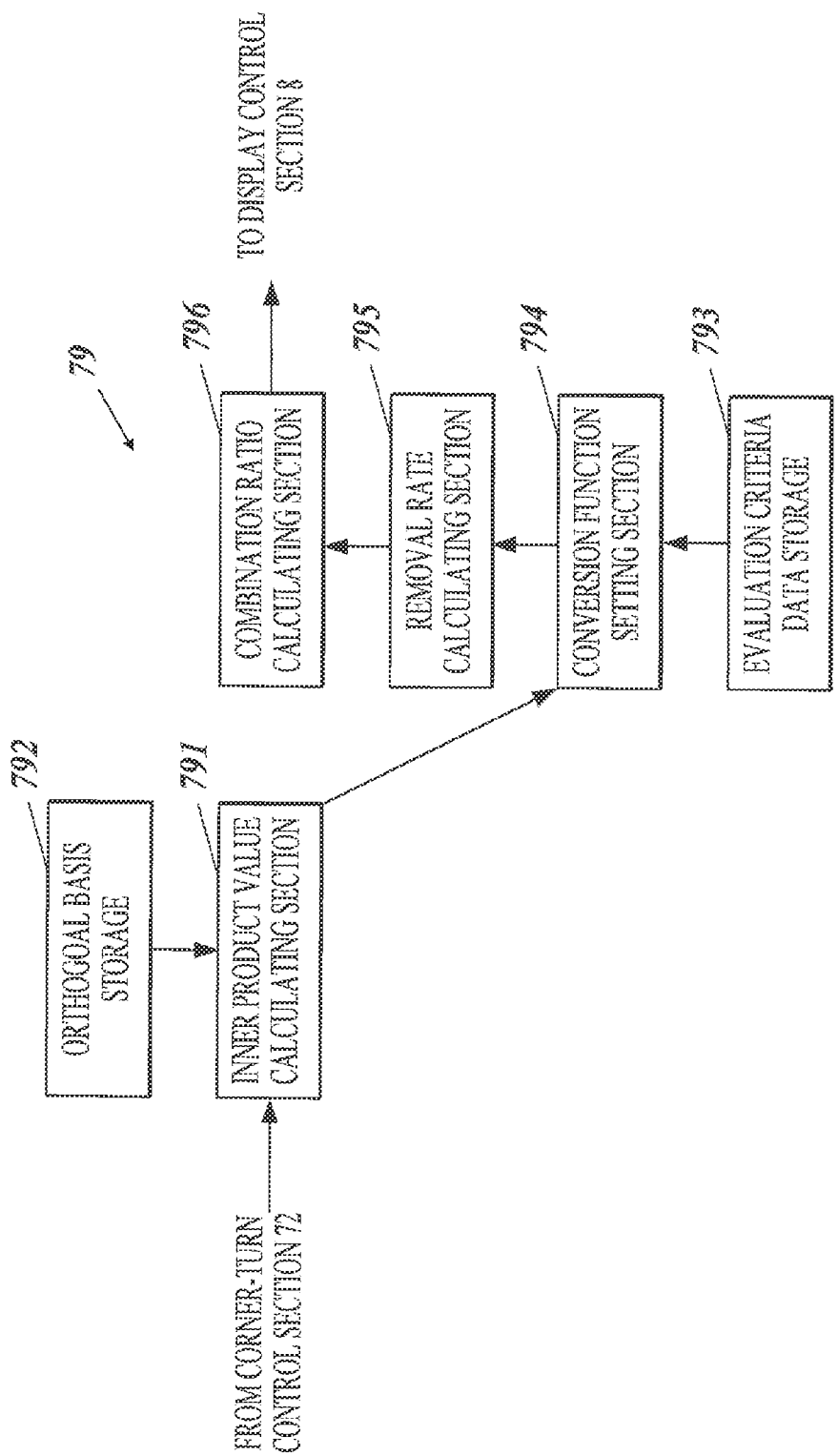
FIG. 18 is a block diagram showing the functional structure of a combination ratio setting section.

The second embodiment of the present invention is described hereinafter with reference to FIGS. 17 to 19. First, the device structure of the present embodiment is explained hereinafter with reference to FIGS. 17 and 18. FIG. 17 is a block diagram showing the functional structure of a C-mode image generating section 7C. FIG. 18 is a block diagram showing the functional structure of a combination ratio setting section 79.

The ultrasound diagnostic device 1 in the first embodiment described above is used as the device structure of the present modification example. However, the C-mode image generating section 7 is substituted by the C-mode image generating section 7C in FIG. 17. The explanation is, therefore, focused on the elements different from the first embodiment. The same elements share the numbering in the drawings, and their descriptions are omitted.

The internal structure of C-mode image generating section 7C is hereinafter explained with reference to FIG. 17. As shown in FIG. 17, the C-mode image generating section 7 has a quadrature detector 71, a corner-turn control section 72, an MTI filter 73C, a correlation calculating section 74, a data converting section 75, a noise removal spatial filtering section 76, an inter-frame filter 77, a C-mode image converting section 78, and a combination ratio setting section 79.

The MTI filter 73C does not use the inner product value Pr like the MTI filters 73, 73A, and 73B in the first embodiment and its first and second modification examples described above, but it is a normal MTI filter using the orthonormal basis. The MTI filter 73C, however, does not necessarily use the orthonormal basis. The MTI filter 73C removes the clutter components by filtering the Doppler signals I and Q input from the corner-turn control section 72 under the control of the control section 9.

The combination ratio setting section 79 calculates the combination ratio α (0 to 1) of the B-mode image in combining the B-mode image and the C-mode image from the Doppler signals I and Q (packet data Sp) input from the corner-turn control section 72 and outputs it to the display processing section 8, under the control by the control section 9. The combination ratio of the C-mode image is given by (1-α). The combination ratio α is a ratio being set for each spatial location (xc, yc) in the ROI (C-mode image).

As shown in FIG. 18, the combination ratio setting section 79 has an inner product calculating section 791 as an inner product value obtaining section, an orthogonal basis storage 792, an evaluation criteria data storage 793, a conversion function setting section 794, a removal rate calculating section 795 as a removal rate obtaining section, and a combination ratio calculating section 796 as a combination ratio obtaining section.

The inner product value calculating section 791, the orthogonal basis storage 792, the evaluation criteria data storage 793, the conversion function setting section 794, and the removal rate calculating section 795 are respectively the same as the inner product value calculating section 731, the orthogonal basis storage 732, the evaluation criteria data storage 733, the conversion function setting section 734, and removal rate calculating section 735 in the first embodiment.

The combination ratio calculating section 796 calculates the combination ratio α of the B-mode image at a spatial location of the C-mode image with the removal rate Rf input from the removal rate calculating section 795, under the control by the control section 9.

At the locations where the packet data contain a lot of clutter, it is better to show the B-mode image without a blood flow image imposed on it in order to increase visibility for the operator (with larger α). It can also decrease misrecognition where the clutter noise is taken for the blood flow.

In the present embodiment, the indicator to decide the locations where the packet data seem to contain a lot of clutter is obtained with the removal rates for all degrees obtained for the packet data. For example, the removal rates for all degrees are calculated and their average removal rate is set as α. The high average of the removal rates indicates that clutter is contained for a lot of degrees. The combination ratio α is then high and the B-mode image is combined at a high ratio. Eventually the clutter is not visible to the operator.

When the B-mode is selected, the display processing section 8 includes in the display image data the B-mode image of the B-mode image data generated in the B-mode image generating section 5 and outputs it to the display 12. When the C-mode is selected, the display processing section 8 multiplies the B-mode image generated in the B-mode image generating section 5 by the combination ratio α input from the combination ratio calculating section 796 at each spatial location, and multiplies the C-mode image generated in the C-mode image generating section 7C by the combination ratio (1-α) at each spatial location. The display processing section 8 combines the B-mode image and C-mode image respectively multiplied by the combination ratios α and (1-α), generates the combined image data, includes the combined image data in the display image data, and outputs it to the display 12.

Next, the combination ratio calculating section 796 of the ultrasound diagnostic device 1 in the present embodiment is described with reference to FIG. 19. FIG. 19 is a flow chart showing the process of calculation of the combination ratio.

The combination ratio setting section 79 executes each process of calculating the combination ratio with each part of the combination ratio setting section 79 under the control of the control section 9. The explanation on the control by the control section 9 is omitted.

As shown in FIG. 19, the steps S51 to S55 in the process of calculating the combination ratio are respectively the same as the steps S11 to S15 in the process of the first MTI filtering in FIG. 11. The steps S51 to S55 are mainly executed respectively by the inner product calculating section 791, the inner product calculating section 791, the conversion function setting section 794, the conversion function setting section 794, and the removal rate calculating section 795.

The combination ratio calculating section 796 calculates the combination ratio α at a spatial location of the C-mode image by the removal rate Rf input from the removal rate calculating section 795, outputs the calculated combination ratio α to the display processing section 8 (Step S56), and then ends the process of calculating the combination ratio.

In accordance with the present embodiment described hereinbefore, the transmitter 3 outputs driving signals for the B-mode image and the C-mode image to the ultrasound probe 101. The receiver 4 obtains reception signals for the B-mode image and the C-mode image from the ultrasound probe 101. The ultrasound diagnostic device 1 has an inner product value calculating section 731 which calculates an inner product value Pr of packet data of a reception signal for the C-mode image and an orthonormal basis $b^H$ for each degree, a combination ratio calculating section 796 which calculates a combination ratio α of the B-mode image to the C-mode image by the removal rate Rf for each degree, a C-mode image converting section 78 which generates C-mode image data from the packet data, and the B-mode image generating section 5 which generates B-mode image data from the reception signal for the B-mode image. The display processing section 8 generates combined image data by combining the B-mode image data and the C-mode image data according to the calculated combination ratio α, and displays a combined image of the combined image data on a display 12.

It can restrain displaying components other than the blood flow (clutter and system noise), improve visibility of blood flow and eventually avoid misdiagnosis.

The above description of the embodiment is an example of the appropriate ultrasound diagnostic device in accordance with the present invention and does not limit the scope of invention. For example, two or more of the embodiments and its modification examples described above and the configurations described hereinafter can be suitably combined. To be concrete, in the second embodiment, the combination ratio α may be generated based on the removal rate Rg in the first modification example, for example, or the combination ratio α may be generated based on the removal rate R in the second modification example.

In the embodiments and modification examples described above, the image data such as the B-mode image data or the combined image data are displayed on the display 12 in the ultrasound diagnostic device 1. However, the configuration is not limited to this and the image data such as the B-mode image data or the combined image data may be stored in the storage 11.

As to the details of the configurations and manners of each part which is incorporated to the ultrasound diagnostic device 1 in accordance with the embodiments described hereinbefore, modifications can be made without departing from the scope of the invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent Application No. 2017-092723, filed on 9 May 2017, is incorporated herein by reference in its entirety.

What is claimed is:

1. An ultrasound diagnostic device comprising:

a transmitter that outputs a C-mode driving signal to an ultrasound probe for generating a C-mode image, wherein the ultrasound probe sends and receives ultrasound;

a receiver that obtains a C-mode reception signal from the ultrasound probe for generating the C-mode image; and a controller that:

calculates an inner product value of packet data of the C-mode reception signal for each degree of a first orthonormal basis;

generates a removal rate based on the inner product value for the each degree to remove a clutter component; and generates C-mode image data from which a signal component of the C-mode image corresponding to the clutter component is removed according to the removal rate for the each degree.

2. The ultrasound diagnostic device according to claim 1, wherein the controller displays on a display the image data from which the signal component of the C-mode image is removed according to the removal rate for the each degree.

3. The ultrasound diagnostic device according to claim 2, wherein the controller calculates filtered packet data by filtering, wherein the filtering includes (1) multiplying the inner product value for the each degree by the removal rate for each degree to obtain a first value, (2) multiplying the first value by a second orthonormal basis which is the Hermitian transpose of the first orthonormal basis to obtain a second value, and (3) subtracting the second value from the packet data to obtain the filtered packet data, the controller generates filtered C-mode image data from the filtered packet data, and the controller displays a filtered C-mode image of the filtered C-mode image data after the filtering on the display.

4. The ultrasound diagnostic device according to claim 2, wherein the transmitter further outputs a B-mode driving signal to the ultrasound probe for generating a B-mode image, the receiver obtains a B-mode reception signal from the ultrasound probe for generating the B-mode image, the controller calculates the inner product value of the packet data of the C-mode reception signal for generating the C-mode image and the first orthonormal basis for the each degree, the controller calculates a combination ratio of the B-mode image to the C-mode image from the removal rate for the each degree, the controller generates the C-mode image data from the packet data, the controller generates B-mode image data from the B-mode reception signal for generating the B-mode image, and the controller generates combined image data by combining the B-mode image data and the C-mode image data according to the calculated combination ratio and displays a combined image of the combined image data on the display.

5. The ultrasound diagnostic device according to claim 1, wherein
the controller calculates an inner product difference value for the each degree between an inner product value for the each degree of a center point of the C-mode image and an inner product value for the each degree of a surrounding region of the center point,
the controller sets a conversion function to convert the inner product difference value for the each degree into the removal rate for the each degree to remove the clutter component, and
the controller converts the inner product difference value for the each degree into the removal rate for each degree by using the set conversion function.

6. The ultrasound diagnostic device according to claim 1, wherein
the controller calculates an inner product difference value between an inner product value for the each degree of a center point of the C-mode image and an inner product value for the each degree of a surrounding region of the center point,
the controller sets (1) a first conversion function to convert the inner product value of the packet data into a first removal rate to remove the clutter component and (2) a second conversion function to convert the inner product difference value into a second removal rate to remove the clutter component,
the controller converts the inner product value for the each degree into the first removal rate for each degree by using the set first conversion function,
converts the inner product difference value for the each degree into the second removal rate for the each degree by using the set second conversion function, and
calculates the removal rate for the each degree from the first removal rate and the second removal rate.

7. The ultrasound diagnostic device according to claim 6, wherein the controller sets a maximum value of the first removal rate for the each degree and the second removal rate for the each degree as the removal rate for the each degree.

8. The ultrasound diagnostic device according to claim 1, wherein the removal rate for the each degree ranges from 0 to 1.

9. The ultrasound diagnostic device according to claim 1, wherein the controller sets a conversion function to convert the inner product value for the each degree into the removal rate for the each degree, and converts the inner product value for the each degree into the removal rate for the each degree by using the conversion function.

10. The ultrasound diagnostic device according to claim 9, wherein the controller sets the conversion function to convert the removal rate for the each degree into 1 when the inner product value for 0 degree is equal to or less than a predetermined threshold value.

11. A method for generating an ultrasound image, the method comprising:
a transmission step of outputting a C-mode driving signal to an ultrasound probe for generating a C-mode image, wherein the ultrasound probe sends and receives ultrasound;
a reception step of obtaining a C-mode reception signal from the ultrasound probe;
an inner product value calculation step of calculating an inner product value of packet data of the C-mode reception signal for each degree of a first orthonormal basis;
a removal rate generating step of generating a removal rate based on the inner product value for the each degree to remove a clutter component; and
a processing step of generating image data from which a signal component of the C-mode image corresponding to the clutter component is removed according to the removal rate for the each degree.

* * * * *